(12) United States Patent
Takeuchi et al.

(10) Patent No.: US 11,090,632 B2
(45) Date of Patent: Aug. 17, 2021

(54) FILTER CONTAINING PHOTOCATALYST PARTICLES AND RESIN PARTICLES

(71) Applicant: FUJIFILM BUSINESS INNOVATION CORP., Tokyo (JP)

(72) Inventors: Sakae Takeuchi, Kanagawa (JP); Hideaki Yoshikawa, Kanagawa (JP); Hiroyoshi Okuno, Kanagawa (JP); Yoshitake Ogura, Kanagawa (JP); Takeshi Iwanaga, Kanagawa (JP)

(73) Assignee: FUJIFILM Business Innovation Corp., Tokyo (JP)

( * ) Notice: Subject to any disclaimer, the term of this patent is extended or adjusted under 35 U.S.C. 154(b) by 0 days.

(21) Appl. No.: 16/363,342

(22) Filed: Mar. 25, 2019

(65) Prior Publication Data

US 2020/0070125 A1  Mar. 5, 2020

(30) Foreign Application Priority Data

Sep. 5, 2018 (JP) .............................. JP2018-165776

(51) Int. Cl.
| | |
|---|---|
| *B01J 21/00* | (2006.01) |
| *B01J 21/08* | (2006.01) |
| *B01J 21/06* | (2006.01) |
| *B01J 31/12* | (2006.01) |
| *B01J 31/06* | (2006.01) |
| *B01J 35/00* | (2006.01) |
| *B01J 35/02* | (2006.01) |
| *A61L 9/20* | (2006.01) |
| *B01J 31/38* | (2006.01) |

(52) U.S. Cl.
CPC .............. *B01J 21/08* (2013.01); *A61L 9/205* (2013.01); *B01J 21/063* (2013.01); *B01J 31/06* (2013.01); *B01J 31/126* (2013.01); *B01J 31/38* (2013.01); *B01J 35/004* (2013.01); *B01J 35/0013* (2013.01); *B01J 35/026* (2013.01); *A61L 2209/14* (2013.01)

(58) Field of Classification Search
CPC .. B01J 21/00; B01J 31/00; B01J 35/00; A61L 9/00; A61L 2209/00
USPC .......................................................... 502/242
See application file for complete search history.

(56) References Cited

U.S. PATENT DOCUMENTS 5,919,422 A * 7/1999 Yamanaka ............... A61L 2/232
  422/121
6,306,343 B1 * 10/2001 Sugiyama .............. B01J 21/063
  422/4

(Continued)

FOREIGN PATENT DOCUMENTS

| CN | 2640468 Y | * | 9/2004 | |
|---|---|---|---|---|
| JP | 2001-246208 A | | 9/2001 | |
| WO | WO-2014116065 A1 | * | 7/2014 | ............... A61L 9/00 |

OTHER PUBLICATIONS

CN-2640468-Y—English translation (Year: 2003).*

*Primary Examiner* — Stefanie J Cohen
(74) *Attorney, Agent, or Firm* — Oliff PLC

(57) ABSTRACT

A filter includes resin particles and photocatalyst particles having absorption at wavelengths of 450 nm and 750 nm in the visible absorption spectrum. The photocatalyst particles have a high photocatalytic function and are present on the surface of the resin particle. The filter is air permeable, transmits visible light, and has high deodorizing performance.

17 Claims, 3 Drawing Sheets

(56) References Cited

U.S. PATENT DOCUMENTS

| | | | | |
|---|---|---|---|---|
| 7,820,100 B2* | 10/2010 | Garfield | ............... | B01J 37/0217 |
| | | | | 422/1 |
| 2002/0005145 A1* | 1/2002 | Sherman | ................ | B01J 21/06 |
| | | | | 106/436 |
| 2003/0050196 A1* | 3/2003 | Hirano | ................... | B01J 35/004 |
| | | | | 507/238 |
| 2009/0032390 A1* | 2/2009 | Osterlund | .............. | B01D 53/88 |
| | | | | 204/157.3 |
| 2010/0304954 A1* | 12/2010 | Sogabe | ................... | B01J 23/30 |
| | | | | 502/5 |
| 2011/0212832 A1* | 9/2011 | Nakano | .................... | C09D 7/69 |
| | | | | 502/305 |
| 2015/0266013 A1* | 9/2015 | Leung | ................... | B01J 19/127 |
| | | | | 204/157.3 |
| 2016/0256583 A1* | 9/2016 | Yamada | ............. | B01J 20/28047 |
| 2018/0147572 A1* | 5/2018 | Fukumura | ................ | B01J 23/30 |
| 2018/0162887 A1* | 6/2018 | Okuno | ................... | B01J 21/063 |

\* cited by examiner

FILTER CONTAINING PHOTOCATALYST PARTICLES AND RESIN PARTICLES

CROSS-REFERENCE TO RELATED APPLICATIONS

This application is based on and claims priority under 35 USC 119 from Japanese Patent Application No. 2018-165776 filed Sep. 5, 2018.

BACKGROUND

(i) Technical Field

The present disclosure relates to a filter.

(ii) Related Art

One of known air or water purification methods involves decomposition and removal of contaminants and odor substances by using a photocatalytic effect. There have been proposed various purification apparatuses that include, for example, a filter carrying a photocatalyst, such as anatase-type titanium oxide, on the surface of a fiber, such as a nonwoven fabric. The filter decomposes, when irradiated with UV rays, contaminants and odor substances adsorbed onto the filter.

As the filter carrying a photocatalyst, for example, a "filter having a photocatalyst particle-containing resin layer on the wall surface" has been disclosed. For example, Japanese Patent Application Laid-Open No. 2001-246208 discloses a filter obtained by attaching a photocatalyst on the surface of a fiber, such as a synthetic fiber, a natural fiber, or a mixture thereof, by using at least one binder resin selected from alkyl silicate-based resins, silicone-based resins, and fluorocarbon-based resins.

SUMMARY

However, the "filter having a photocatalyst particle-containing resin layer on the wall surface" may have a low photocatalytic function because the resin covers the surface of the photocatalyst particles to reduce the area of the exposed photocatalyst particles. There is thus a need to provide a filter having higher deodorizing performance than the filter having a photocatalyst particle-containing resin layer on the wall surface.

Aspects of non-limiting embodiments of the present disclosure relate to a filter having higher deodorizing performance than a filter having a photocatalyst particle-containing resin layer on the wall surface.

Aspects of certain non-limiting embodiments of the present disclosure address the above advantages and/or other advantages not described above. However, aspects of the non-limiting embodiments are not required to address the advantages described above, and aspects of the non-limiting embodiments of the present disclosure may not address advantages described above.

According to an aspect of the present disclosure, there is provided a filter including resin particles, and photocatalyst particles having absorption at wavelengths of 450 nm and 750 nm in a visible absorption spectrum, wherein the photocatalyst particles are present on a surface of each resin particle.

BRIEF DESCRIPTION OF THE DRAWINGS

Exemplary embodiments of the present disclosure will be described in detail based on the following figures, wherein.

DETAILED DESCRIPTION

Figure 1:
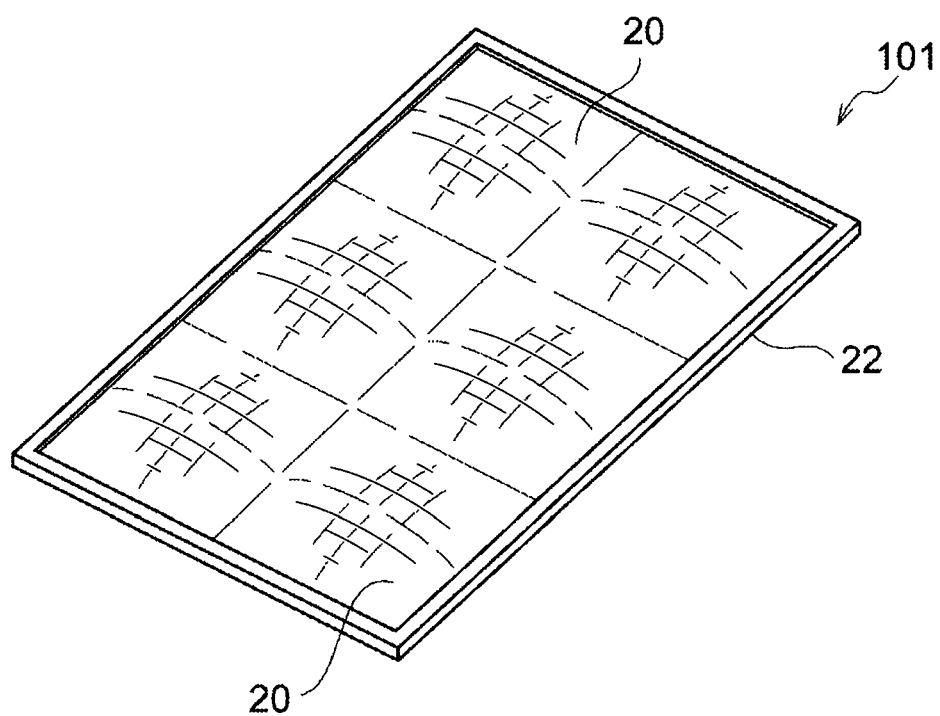
FIG. 1 is a schematic perspective view of an example of a filter according to an exemplary embodiment.

Exemplary embodiments of the present disclosure will be described below. The following description and Examples are provided to illustrate exemplary embodiments of the present disclosure but are not intended to limit the scope of the present disclosure.

In this specification, the amount of a component in a composition refers to, when there are several substances corresponding to the component in the composition, the total amount of the substances present in the composition, unless otherwise specified.

The term "step" not only includes an independent step but also includes a step that, even if cannot be clearly distinguished from other steps, accomplishes an intended purpose of the step.

The term "XPS" is an acronym for X-ray Photoelectron Spectroscopy.

A filter according to an exemplary embodiment includes resin particles with the surface to which photocatalyst particles having absorption at wavelengths of 450 nm and 750 nm in a visible absorption spectrum are attached (the resin particles may also be referred to as "catalyst-attached resin particles" in this specification).

The filter according to the exemplary embodiment has good deodorizing performance. The reason for this is as described below.

To impart a deodorizing function to a filter, the use of photocatalyst particles with a large surface area is effective. However, there is a need to provide a filter having higher deodorizing performance than a filter having a photocatalyst particle-containing resin layer on the wall surface. The photocatalyst particles that actually function as a photocatalyst come from limited particles exposed from the resin layer.

The photocatalyst particles are attached to the resin particles, for example, electrostatically, by means of the adhesive strength of the surface, or in a partially embedded manner. In other words, the area of the exposed photocatalyst particles is large. Thus, the photocatalyst particles present on the entire surface of the resin particle actually function as a photocatalyst.

In addition, photocatalyst particles having absorption at wavelengths of 450 nm and 750 nm in the visible absorption spectrum have a high photocatalytic function in the visible light region. Therefore, when visible light reaches the photocatalyst-attached resin particles, the photocatalyst particles present on the entire surface of the resin particle actually function as a photocatalyst.

Since the photocatalyst particles attached to the surface actually function as a photocatalyst in the catalyst-attached resin particles, the filter having the catalyst-attached resin particles efficiently exhibits a deodorizing function attributed to the photocatalytic function.

As described above, the filter according to the exemplary embodiment has good deodorizing performance.

In the filter according to the exemplary embodiment, the dispersibility and adhesion of the photocatalyst particles with respect to the resin particles are increased by using, as photocatalyst particles, highly hydrophobic particles that have been subjected to the surface treatment described below. The detachment of the photocatalyst particles is thus prevented or reduced. As a result, the filter according to the exemplary embodiment has high ability to maintain its deodorizing performance.

An example of the filter according to the exemplary embodiment will be described below with reference to the drawings.

Figure 2:
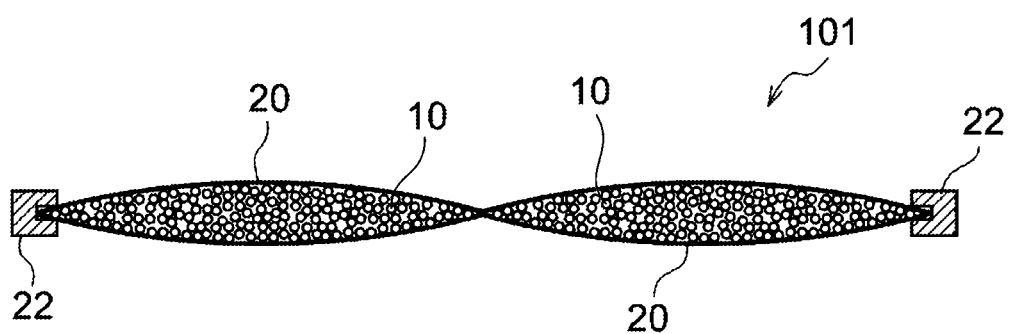
FIG. 2 is a schematic sectional view of an example of the filter according to the exemplary embodiment.
Figure 3:
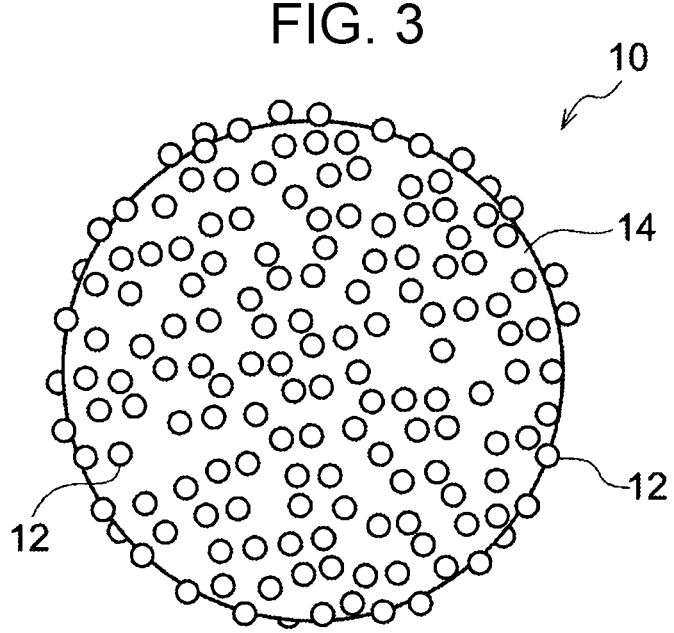
FIG. 3 is a schematic structural view of an example of a catalyst-attached resin particle in the filter according to the exemplary embodiment.

As illustrated in FIG. 1 to FIG. 3, a filter 101 according to an exemplary embodiment includes catalyst-attached resin particles 10 and a holding member 20 that holds the catalyst-attached resin particles 10.

Holding Member 20

The holding member 20 is formed of, for example, a bag-shaped member or a box-shaped member. The holding member 20 may be a member that has a filter function by itself.

The bag-shaped member or box-shaped member is a member for holding (that is, enclosing) the catalyst-attached resin particles 10 inside.

Examples of the bag-shaped member include a member produced by forming an air-permeable, liquid-permeable, flexible sheet into a bag shape.

Examples of the box-shaped member include a member produced by forming an air-permeable, liquid-permeable, rigid sheet into a box shape. Examples of the box-shaped member include a member produced by attaching an air-permeable, liquid-permeable, flexible sheet to each surface of a rigid frame body.

When the holding member 20 has no self-supporting property, a frame body 22 for supporting the holding member 20 may be provided at the periphery of the holding member 20.

Examples of the material of the holding member 20 include fibrous materials, porous resin bodies (e.g., porous resin membrane, and sponge), porous metal bodies, and porous ceramic bodies.

Examples of fibrous materials include textiles, knitted fabrics, and nonwoven fabrics. Examples of suitable fibrous materials include textiles or knitted fabrics made of cotton, silk, polyester fiber, nylon fiber and the like; and nonwoven fabrics made of cotton, polyester fiber, polyethylene fiber, polypropylene fiber, acrylic fiber, nylon fiber, vinylon fiber, cellulose fiber, aramid fiber, glass fiber, and the like. In view of the filter performance of a filter 110, such as air permeability, liquid permeability, flexibility, rigidity, and ease of adhesion of photocatalyst particles, the fiber diameter of the fibrous material is preferably 0.5 μm or more and 50 μm or less, and more preferably 1 μm or more and 20 μm or less.

Examples of porous resin bodies include porous resin membranes made of polyvinylidene fluoride (PVDF), poly- tetrafluoroethylene (PTFE), polyethersulfone, and the like; and sponges made of urethane, polypropylene, and the like.

Examples of paper include filter paper made of cellulose.

Examples of porous metal bodies include a porous metal body produced by sintering a metal or alloy, such as SUS, aluminum, or nickel.

Examples of porous ceramic bodies and the like include a porous ceramic body produced by sintering a ceramic.

Among these, fibrous materials, such as textiles, knitted fabrics, and nonwoven fabrics, which have a high filter effect, are preferred.

The average opening diameter of the holding member 20 is, for example, smaller than the particle size of the catalyst-attached resin particles 10 to prevent or reduce the detachment of the catalyst-attached resin particles 10.

Specifically, the average opening diameter of the holding member 20 is preferably 0.5 μm or more and 30 μm or less, and more preferably 1 μm or more and 20 μm or less.

The average opening diameter of the holding member 20 is measured in the following manner.

The image of the holding member 20 is captured by observation under a scanning electron microscope (S-4100 available from Hitachi, Ltd.). In this case, the image is captured with the scanning electron microscope at a magnification adjusted so as to observe plural openings of the holding member 20, and the opening diameter is determined.

For example, when the holding member 20 is formed of a porous body, such as a porous resin body, the opening has an elliptical shape or an irregular shape, and thus the major axis (that is, maximum diameter) of the opening is taken as an opening diameter.

For example, when the holding member 20 is formed of a fibrous material, such as a nonwoven fabric or a textile, each opening is formed by interlacing fibers, and thus the maximum diameter of an opening (that is, a gap through which the back side can be seen from the front side) that penetrates in the thickness direction is taken as an opening diameter.

The opening diameter is measured at 10 to 50 points, and the mean is taken as an average opening diameter.

The holding member 20 may be divided in a planar lattice shape in order to prevent the uneven distribution of the enclosed catalyst-attached resin particles 10. The shape of the divided region is not limited to a lattice shape and may be any shape, such as a planar rhombus shape.

The holding member 20 is not necessarily a bag-shaped member or box-shaped member, but may be a planar member having air permeability and liquid permeability (e.g., a monolayer body or multilayer body formed of a fibrous material, a porous resin body (e.g., a porous resin membrane, or sponge), a porous metal body, a porous ceramic body, or the like). In this case, the filter is, for example, a planer member having catalyst-attached resin particles, which is produced by impregnating a planer member with a dispersion containing catalyst-attached resin particles and drying the dispersion.

Catalyst-Attached Resin Particles

The catalyst-attached resin particles 10 are resin particles 14 having the surface to which photocatalyst particles 12 are attached.

Figure 4:
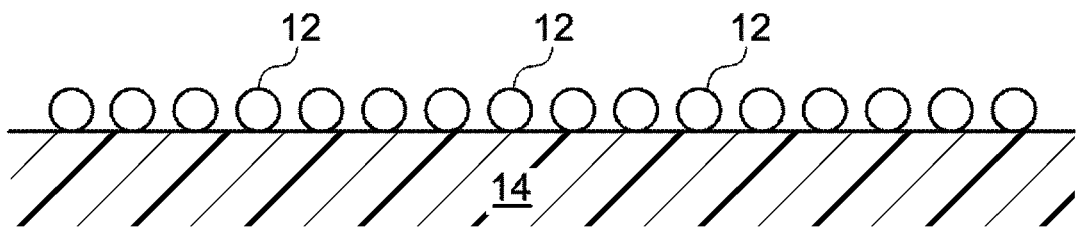
FIG. 4 is a schematic structural view for illustrating the state of photocatalyst particles attached to a resin particle in the catalyst-attached resin particle.
Figure 5:
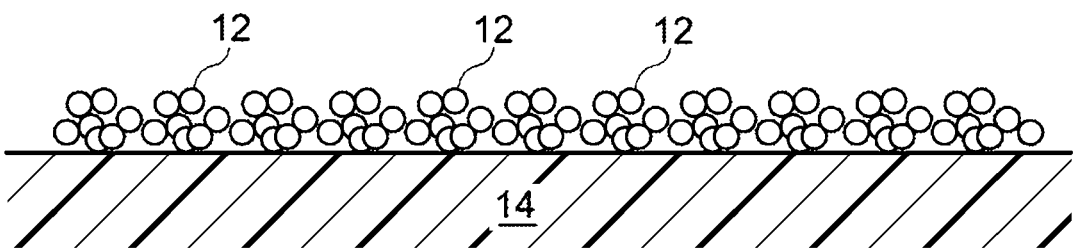
FIG. 5 is a schematic structural view for illustrating the state of the photocatalyst particles attached to the resin particle in the catalyst-attached resin particle.

When the photocatalyst particles 12 are metatitanic acid particles or titanium oxide particles, as illustrated in FIG. 4, the photocatalyst particles 12 in the form of primary particles may be attached to the surface of a resin particle 14. When the photocatalyst particles 12 are titanium oxide aerogel particles and silica-titania composite aerogel particles, as illustrated in FIG. 5, the photocatalyst particles 12 in the form of aggregates having an aerogel structure may be attached to the surface of the resin particle 14.

The term "aerogel structure" refers to the structure of aggregated primary particles forming a porous structure and indicates an internally three-dimensional mesh-like fine structure having a cluster structure formed by assembled particle-like materials with a nanometer order size.

The photocatalyst particles 12 and the resin particles 14 will be described below in detail. The description will be given without reference numerals.

Photocatalyst Particles

The photocatalyst particles have absorption at wavelengths of 450 nm and 750 nm in the visible absorption spectrum. Accordingly, the photocatalyst particles have a high photocatalytic function driven by visible light.

Specifically, the photocatalyst particles may be particles having the surface to which a metal compound having a metal atom and a hydrocarbon group is bonded via an oxygen atom.

The particles having the surface to which a metal compound having a metal atom and a hydrocarbon group is bonded via an oxygen atom are prepared as follows: for example, treating the surfaces of untreated particles (e.g., untreated metatitanic acid particles, untreated titanium oxide particles, untreated titanium oxide aerogel particles, and untreated silica-titania composite aerogel particles) with a metal compound having a hydrocarbon group; and oxidizing at least part of the hydrocarbon group by a heat treatment into C—O bonds or C=O bonds. Although the detailed mechanism is unclear, the surfaces of the particles exhibits light absorption at wavelengths of 450 nm and 750 nm due to the presence of the structure formed, on the surfaces of the particles, by sequentially bonding an organometallic compound having appropriately oxidized carbon atoms, an oxygen atom, and a titanium atom (or silicon atom) to each other through covalent bonds. Accordingly, the particles may exhibit a visible light-driven photocatalytic function (visible-light responsiveness).

Hereafter, the metal compound having a metal atom and a hydrocarbon group is also referred to simply as an "organometallic compound."

The photocatalyst particles not only exhibit a high photocatalytic function even in the visible light region but also have the following features.

In general, untreated particles (e.g., untreated metatitanic acid particles, untreated titanium oxide particles, untreated titanium oxide aerogel particles, and untreated silica-titania composite aerogel particles) have high hydrophilicity and high aggregability and thus tend to have poor dispersion and adhesion with respect to resin particles.

When the surfaces of the photocatalyst particles have a hydrocarbon group derived from an organometallic compound, the photocatalyst particles have higher hydrophobicity and have improved dispersibility and adhesion with respect to resin particles. Thus, the photocatalyst particles are substantially uniformly attached to the surface of the resin particle and unlikely to be detached from the resin particles.

Untreated Particles

Examples of particles (untreated particles) to be subjected to the surface treatment with an organometallic compound include untreated titanium compound particles. Examples of untreated titanium compound particles include untreated particles, such as untreated metatitanic acid particles, untreated titanium oxide particles, untreated titanium oxide aerogel particles, and untreated silica-titania composite aerogel particles. In other words, the photocatalyst particles may be at least one type of particles selected from the group consisting of metatitanic acid particles, titanium oxide particles, and silica-titania composite particles.

When photocatalyst particles in the form of aggregates having an aerogel structure are attached to the surface of the resin particle, untreated titanium compound particles may be at least one type of particles selected from untreated titanium oxide aerogel particles and untreated silica-titania composite aerogel particles.

Untreated Metatitanic Acid Particles

The untreated metatitanic acid particles refer to titanic acid particles of titanic acid hydrate $TiO_2 \cdot nH_2O$ where $n=1$.

Examples of the method for producing untreated metatitanic acid particles include, but are not limited to, a chlorine method (gas phase method) and a sulfuric acid method (liquid phase method). A sulfuric acid method is preferred.

An example of the sulfuric acid method (liquid phase method) is as follows. First, ilmenite ore ($FeTiO_3$) or titanium slag, which is a raw material, is dissolved in concentrated sulfuric acid, and the iron component, which is an impurity, is separated in the form of iron sulfate ($FeSO_4$) to form titanium oxysulfate ($TiOSO_4$) (titanyl sulfate solution). Next, titanium oxysulfate ($TiOSO_4$) is hydrolyzed to produce untreated metatitanic acid [titanium oxyhydroxide ($TiO(OH)_2$)] particles.

Untreated Titanium Oxide Particles

Examples of the untreated titanium oxide particles include brookite-type, anatase-type, and rutile-type titanium oxide particles. The titanium oxide particles may have a single-crystal structure, such as brookite, anatase, or rutile, or may have a mixed crystal structure where these crystals are present together.

Examples of the method for producing untreated titanium oxide particles include, but are not limited to, a chlorine method (gas phase method) and a sulfuric acid method (liquid phase method).

Untreated Titanium Oxide Aerogel Particles

The untreated titanium oxide aerogel particles may be produced by a sol-gel method using a titanium alkoxide as a material.

The untreated titanium oxide aerogel particles may be formed of a hydrolysis-condensation product of the titanium alkoxide. Some of the alkoxy groups of the titanium alkoxide may remain unreacted in the particles.

The method for producing the untreated titanium oxide aerogel particles will be described below.

The method for producing the untreated titanium oxide aerogel particles may include at least the following steps (1) and (2).

(1) A step of making porous particles containing titanium oxide by a sol-gel method to prepare a dispersion containing the porous particles and a solvent (dispersion preparing step).

(2) A step of removing the solvent from the dispersion by using supercritical carbon dioxide (solvent removing step).

(1) Dispersion Preparing Step

The dispersion preparing step involves, for example, causing the reactions (hydrolysis and condensation) of a titanium alkoxide, which is used as a material, to generate titanium oxide, forming a dispersion in which porous particles containing the titanium oxide are dispersed in a solvent.

The dispersion preparing step is specifically, for example, the following step.

A titanium alkoxide is added to an alcohol and, under stirring, an acid aqueous solution is added dropwise thereto to cause the reaction of the titanium alkoxide and thus to generate titanium oxide, forming a dispersion (porous particle dispersion) in which porous particles containing titanium oxide are dispersed in the alcohol.

Here, the primary particle size of the porous particles can be controlled by the amount of the titanium alkoxide added in the dispersion preparing step. A larger amount of the titanium alkoxide added results in a smaller primary particle size of the porous particles. The mass ratio of the titanium alkoxide to the alcohol is preferably 0.04 or more and 0.65 or less, and more preferably 0.1 or more and 0.5 or less.

Examples of the titanium alkoxide used in the dispersion preparing step include tetraalkoxytitaniums, such as tetramethoxytitanium, tetraethoxytitanium, tetrapropoxytitanium, and tetrabutoxytitanium; alkoxy titanium chelates in which some of alkoxy groups are chelated, such as di-i-propoxy.bis (ethylacetate)titanium, and di-i-propoxy.bis(acetylacetonato)titanium. These titanium alkoxides may be used alone or in combination of two or more.

The titanium oxide aerogel particles may contain a small amount of a metal element other than titanium, such as silicon and aluminum. In this case, a tetraalkoxysilane, such as tetramethoxysilane, tetraethoxysilane, tetrapropoxysilane, or tetrabutoxysilane; an alkyltrialkoxysilane, such as methyltrimethoxysilane, methyltriethoxysilane, or ethyltriethoxysilane; an alkyldialkoxysilane, such as dimethyldimethoxysilane or dimethyldiethoxysilane; or an aluminum alkoxide, such as aluminum isopropoxide may be used. When the titanium oxide aerogel particles contain a silicon element, these substances can be used at an elemental ratio Si/Ti of silicon to titanium in the range from 0 to 0.05.

Examples of the alcohol used in the dispersion preparing step include methanol, ethanol, propanol, and butanol. These alcohols may be used alone or in combination of two or more.

Examples of the acid for the acid aqueous solution used in the dispersion preparing step include oxalic acid, acetic acid, hydrochloric acid, and nitric acid. The acid concentration of the acid aqueous solution is preferably 0.001 mass % or more and 1 mass % or less, and more preferably 0.005 mass % or more and 0.01 mass % or less.

The amount of the acid aqueous solution added dropwise in the dispersion preparing step is preferably 0.001 parts by mass or more and 0.1 parts by mass or less relative to 100 parts by mass of the titanium alkoxide.

The solid content of the porous particle dispersion prepared in the dispersion preparing step is preferably 1 mass % or more and 30 mass % or less.

(2) Solvent Removing Step

The solvent removing step involves bringing supercritical carbon dioxide into contact with a dispersion containing porous particles and a solvent to remove the solvent. The solvent removing process using supercritical carbon dioxide is less likely to cause closing or clogging of pores of the porous particles than a solvent removing process performed by heating. When the solvent removing step is a step of removing the solvent by using supercritical carbon dioxide, titanium oxide aerogel particles having a BET specific surface area of 120 m$^2$/g or more can be obtained.

The solvent removing step is specifically performed by, for example, using the following process.

To a sealed reactor, the porous particle dispersion is placed, and liquefied carbon dioxide is next introduced. The sealed reactor is then heated, and the pressure in the sealed reactor is increased with a high-pressure pump to bring carbon dioxide in the sealed reactor into the supercritical state. Liquefied carbon dioxide is then introduced into the sealed reactor to discharge supercritical carbon dioxide from the sealed reactor, and supercritical carbon dioxide is circulated in the porous particle dispersion in the sealed reactor accordingly. During the circulation of supercritical carbon dioxide in the porous particle dispersion, the solvent is dissolved in supercritical carbon dioxide and removed together with supercritical carbon dioxide discharged from the sealed reactor.

The temperature and the pressure in the sealed reactor correspond to the temperature and the pressure at which carbon dioxide is converted into the supercritical state. Since the critical point of carbon dioxide is at 31.1° C./7.38 MPa, the temperature and the pressure are, for example, 50° C. or higher and 200° C. or lower/10 MPa or more and 30 MPa or less.

Untreated Silica-Titania Composite Aerogel Particles

The untreated silica-titania composite aerogel particles contain a silica-titania composite, which is a silica-titanium composite oxide, as a main component (the greatest proportion of component among all particle components).

The elemental ratio Si/Ti of silicon to titanium in the untreated silica-titania composite aerogel particles is preferably more than 0 and 6 or less, more preferably 0.05 or more and 4 or less, and still more preferably 0.1 or more and 3 or less in order to exhibit a photocatalytic function in the visible light region.

The elemental ratio (Si/Ti) of silicon atoms to titanium atoms is determined on the basis of the elemental profiles for the silica-titania composite created by XPS qualitative analysis (wide scan analysis). Specifically, the elemental ratio (Si/Ti) is determined as described below.

The identification and quantitative determination of titanium atoms, silicon atoms, and carbon atoms are performed by qualitative analysis (wide scan analysis) involving etching the silica-titania composite in the depth direction from the surface by using an XPS analyzer under the following conditions. From the obtained data, the elemental profiles where the vertical axis indicates peak intensity and the horizontal axis indicates etching time are drawn for titanium atoms, silicon atoms, and carbon atoms. Each profile curve is divided into plural regions at inflection points. The region (region A described below) where the peak intensity of titanium atoms and the peak intensity of silicon atoms are substantially constant) is specified, and the elemental ratio Si/Ti in the region is determined.

XPS analyzer: available from Ulvac-Phi, Incorporated, Versa Probe II
X-ray source: monochromatic Al Kα rays
Acceleration voltage: 15 kV
X-ray beam diameter: 100 μm
Etching gun: argon ion beam
Etching output: 4 kV In the untreated silica-titania composite aerogel particles, the total amount of the silica component and the titania component is preferably 80 mass % or more, more preferably 90 mass % or more, and still more preferably 95 mass % or more relative to the total mass of the composite.

The untreated silica-titania composite aerogel particles may include base particles having an elemental ratio Si/Ti of silicon to titanium of more than 0 and 6 or less, and a titania layer (layer made of titania) present on the surface of the base particles. In other words, the untreated silica-titania composite aerogel particles may be particles having a titania layer on its surface layer. The use of these particles may improve the photocatalytic function.

The method for producing the untreated silica-titania composite aerogel particles may be a sol-gel method using an alkoxy silane and a titanium alkoxide as materials.

The untreated silica-titania composite aerogel particles may be formed of a hydrolysis-condensation product of an alkoxy silane and a titanium alkoxide. However, some of hydrocarbon groups, such as alkoxy groups, of the alkoxy silane or the titanium alkoxide may remain unreacted in the composite.

The method for producing the untreated silica-titania composite aerogel particles will be described below.

The method for producing the untreated silica-titania composite aerogel particles may include at least the following steps (1') and (2').

(1') A step of making porous particles containing a silica-titania composite by a sol-gel method to prepare a dispersion containing the porous particles and a solvent (dispersion preparing step).

(2') A step of removing the solvent from the dispersion by using supercritical carbon dioxide (solvent removing step).

(1') Dispersion Preparing Step

The dispersion preparing step involves, for example, causing the reactions (hydrolysis and condensation) of an alkoxy silane and a titanium alkoxide, which are used as materials, to generate a silica-titania composite, forming a dispersion in which porous particles containing the silica-titania composite are dispersed in a solvent. Here, the porous particles may be aggregated particles generated by aggregating primary particles that contain the silica-titania composite and form a porous structure.

The dispersion preparing step is specifically, for example, the following step.

An alkoxy silane and a titanium alkoxide are added to an alcohol and, under stirring, an acid aqueous solution is added dropwise thereto to cause the reaction of the alkoxy silane and the titanium alkoxide and thus to generate a silica-titania composite, forming a dispersion (porous particle dispersion) in which porous particles containing the silica-titania composite are dispersed in the alcohol.

The elemental ratio Si/Ti of silicon and titanium in the untreated silica-titania composite aerogel particles can be controlled by adjusting the mixing ratio of the alkoxy silane and the titanium alkoxide in the dispersion preparing step.

The particle size of the primary particles forming the untreated silica-titania aerogel particles and the particle size of the untreated silica-titania aerogel particles can be controlled by the total amount of the alkoxy silane and the titanium alkoxide relative to the amount of the alcohol in the dispersion preparing step. As the total amount relative to the amount of the alcohol increases, the particle size of the primary particles forming the untreated silica-titania composite aerogel particles decreases, and the particle size of the untreated silica-titania composite aerogel particles increases. The total amount of the alkoxy silane and the titanium alkoxide is preferably 4 parts by mass or more and 250 parts by mass or less, and more preferably 10 parts by mass or more and 50 parts by mass or less relative to 100 parts by mass of the alcohol.

Examples of the alkoxy silane used in the dispersion preparing step include tetraalkoxysilanes, such as tetramethoxysilane, tetraethoxysilane, tetrapropoxysilane, and tetrabutoxysilane; alkyltrialkoxysilanes, such as methyltrimethoxysilane, methyltriethoxysilane, and ethyltriethoxysilane; and dialkyldialkoxysilanes, such as dimethyldimethoxysilane and dimethyldiethoxysilane. These alkoxy silanes may be used alone or in combination of two or more.

Examples of the titanium alkoxide used in the dispersion preparing step include tetraalkoxytitaniums, such as tetramethoxytitanium, tetraethoxytitanium, tetrapropoxytitanium, and tetrabutoxytitanium; and alkoxy titanium chelates in which some of alkoxy groups are chelated, such as di-i-propoxy.bis(ethylacetoacetate)titanium, and di-i-propoxy.bis(acetylacetonato)titanium. These titanium alkoxides may be used alone or in combination of two or more.

Examples of the alcohol used in the dispersion preparing step include methanol, ethanol, propanol, and butanol. These alcohols may be used alone or in combination of two or more.

Examples of the acid for the acid aqueous solution used in the dispersion preparing step include oxalic acid, acetic acid, hydrochloric acid, and nitric acid. The acid concentration of the acid aqueous solution is preferably 0.001 mass % or more and 1 mass % or less, and more preferably 0.005 mass % or more and 0.01 mass % or less.

The amount of the acid aqueous solution added dropwise in the dispersion preparing step is preferably 0.001 parts by mass or more and 0.1 parts by mass or less relative to 100 parts by mass of the total amount of the alkoxy silane and the titanium alkoxide.

The solid content of the porous particle dispersion prepared in the dispersion preparing step is preferably 1 mass % or more and 30 mass % or less.

(2') Solvent Removing Step

The solvent removing step involves bringing supercritical carbon dioxide into contact with a dispersion containing porous particles and a solvent to remove the solvent. The solvent removing process using supercritical carbon dioxide is less likely to cause closing or clogging of pores of the porous particles (in particular, aggregated particles generated by aggregating primary particles forming a porous structure) than a solvent removing process performed by heating. When the solvent removing step is a step of removing the solvent by using supercritical carbon dioxide, untreated silica-titania composite aerogel particles having a BET specific surface area of 200 $m^2/g$ or more can be obtained.

The solvent removing step is specifically performed by, for example, using the following process.

To a sealed reactor, the porous particle dispersion is placed, and liquefied carbon dioxide is next introduced. The sealed reactor is then heated, and the pressure in the sealed reactor is increased with a high-pressure pump to bring carbon dioxide in the sealed reactor into the supercritical state. Liquefied carbon dioxide is then introduced into the sealed reactor to discharge supercritical carbon dioxide from the sealed reactor, and supercritical carbon dioxide is circulated in the porous particle dispersion in the sealed reactor accordingly. During the circulation of supercritical carbon dioxide in the porous particle dispersion, the solvent is dissolved in supercritical carbon dioxide and removed together with supercritical carbon dioxide discharged from the sealed reactor.

The temperature and the pressure in the sealed reactor correspond to the temperature and the pressure at which carbon dioxide is converted into the supercritical state. Since the critical point of carbon dioxide is at 31.1° C./7.38 MPa, the temperature and the pressure are, for example, 50° C. or higher and 200° C. or lower/10 MPa or more and 30 MPa or less.

When particles having a titania layer on its surface layer are produced as untreated silica-titania composite aerogel particles, the dispersion preparing step (1') may involve the following operations (i) and (ii).

(i) An alkoxy silane and a titanium alkoxide are added to an alcohol and, under stirring, an acid aqueous solution is added dropwise thereto to cause the reaction of the alkoxy silane and the titanium alkoxide and thus to generate a silica-titania composite, forming a dispersion (first dispersion) in which base particles containing the silica-titania composite are dispersed in the alcohol.

(ii) A mixture formed by mixing an alcohol and a titanium alkoxide is added dropwise to the first dispersion under stirring to cause the reaction of the base particles and the titanium alkoxide and thus to generate porous particles having an intermediate layer on the surface of the base particles, forming a dispersion (second dispersion) in which the porous particles are dispersed in the alcohol.

Organometallic Compound

The organometallic compound is a metal compound having a metal atom and a hydrocarbon group.

In order that the organometallic compound easily exhibits visible-light responsiveness, the organometallic compound may be a metal compound having a metal atom, a carbon atom, a hydrogen atom, and an oxygen atom.

In order that the organometallic compound easily exhibits visible-light responsiveness, the organometallic compound may be bonded to the surfaces of the particles via an oxygen atom O directly bonded to the metal atom M in the organometallic compound, that is, may be bonded to the surfaces of the particles through covalent bonds M-O—Ti (or M-O—Si).

In order that the organometallic compound easily exhibits visible-light responsiveness, the organometallic compound may be an organometallic compound having a metal atom M and a hydrocarbon group directly bonded to the metal atom M. The organometallic compound may be bonded to the surfaces of the particles via an oxygen atom O directly bonded to the metal atom M in the organometallic compound. In other words, the surfaces of the particles may have a structure (hydrocarbon group-M-O—Ti (or hydrocarbon group-M-O—Si)) formed by sequentially bonding a hydrocarbon group, a metal atom M, an oxygen atom O, and a titanium atom Ti to each other through covalent bonds, in order that the organometallic compound easily exhibits visible-light responsiveness.

When the organometallic compound has plural hydrocarbon groups, at least one of the hydrocarbon groups may be directly bonded to the metal atom in the organometallic compound.

The chemical bonding state between atoms in the organometallic compound can be determined by high-resolution X-ray Photoelectron Spectroscopy (XPS) analysis (narrow scan analysis).

The metal atom M of the organometallic compound is preferably silicon, aluminum, or titanium, more preferably silicon or aluminum, and still more preferably silicon.

Examples of the hydrocarbon group of the organometallic compound include saturated or unsaturated aliphatic hydrocarbon groups having 1 or more and 40 or less carbon atoms (preferably 1 or more and 20 or less carbon atoms, more preferably 1 or more and 18 or less carbon atoms, still more preferably 4 or more and 12 or less carbon atoms, and yet still more preferably 4 or more and 10 or less carbon atoms), and aromatic hydrocarbon groups having 6 or more and 27 or less carbon atoms (preferably 6 or more and 20 or less carbon atoms, more preferably 6 or more and 18 or less carbon atoms, still more preferably 6 or more and 12 or less carbon atoms, and yet still more preferably 6 or more and 10 or less carbon atoms).

To exhibit a high photocatalytic function and improve dispersibility, the hydrocarbon group of the organometallic compound is preferably an aliphatic hydrocarbon group, more preferably a saturated aliphatic hydrocarbon group, and still more preferably an alkyl group. The aliphatic hydrocarbon group may be a straight-chain, branched-chain, or cyclic hydrocarbon group, but preferably a straight-chain or branched-chain hydrocarbon group in view of dispersibility. The number of carbons in the aliphatic hydrocarbon group is preferably 1 or more and 20 or less, more preferably 1 or more and 18 or less, still more preferably 4 or more and 12 or less, and yet still more preferably 4 or more and 10 or less.

The organometallic compound may be a silane compound having a hydrocarbon group. Examples of the silane compound having a hydrocarbon group include a chlorosilane compound and alkoxy silane compounds.

To exhibit a high photocatalytic function and improve dispersibility, the silane compound having a hydrocarbon group may be a compound represented by formula (1) of $R^1{}_n SiR^2{}_m$.

In formula (1) of $R^1{}_n SiR^2{}_m$, $R^1$ represents a saturated or unsaturated aliphatic hydrocarbon group having 1 or more and 20 or less carbon atoms or an aromatic hydrocarbon group having 6 or more and 20 or less carbon atoms, $R^2$ represents a halogen atom or an alkoxy group, n represents an integer of 1 or more and 3 or less, and m represents an integer of 1 or more and 3 or less, wherein n+m=4. When n is an integer of 2 or 3, plural $R^1$'s may be the same group or different groups. When m is an integer of 2 or 3, plural $R^2$'s may be the same group or different groups.

The aliphatic hydrocarbon group represented by $R^1$ may be a straight-chain, branched-chain, or cyclic hydrocarbon group, but preferably a straight-chain or branched-chain hydrocarbon group in view of dispersibility. To exhibit a high photocatalytic function and improve dispersibility, the number of carbons in the aliphatic hydrocarbon group is preferably 1 or more and 20 or less, more preferably 1 or more and 18 or less, still more preferably 4 or more and 12 or less, and yet still more preferably 4 or more and 10 or less. The aliphatic hydrocarbon group may be saturated or unsaturated. To exhibit a high photocatalytic function and improve dispersibility, the aliphatic hydrocarbon group is preferably a saturated aliphatic hydrocarbon group, and more preferably an alkyl group.

Examples of the saturated aliphatic hydrocarbon group include straight-chain alkyl groups (e.g., a methyl group, an ethyl group, a propyl group, a butyl group, a pentyl group, a hexyl group, a heptyl group, an octyl group, a nonyl group, a decyl group, a dodecyl group, a hexadecyl group, and an icosyl group), branched-chain alkyl groups (e.g., an isopropyl group, an isobutyl group, an isopentyl group, a neopentyl group, a 2-ethylhexyl group, a tertiary butyl group, a tertiary pentyl group, and an isopentadecyl group), and cyclic alkyl groups (e.g., a cyclopropyl group, a cyclopentyl group, a cyclohexyl group, a cycloheptyl group, a cyclooctyl group, a tricyclodecyl group, a norbornyl group, and an adamantyl group).

Examples of the unsaturated aliphatic hydrocarbon group include alkenyl groups (e.g., a vinyl group (ethenyl group), a 1-propenyl group, a 2-propenyl group, a 2-butenyl group, a 1-butenyl group, a 1-hexenyl group, a 2-dodecenyl group, and a pentenyl group), and alkynyl groups (e.g., an ethynyl group, a 1-propynyl group, a 2-propynyl group, a 1-butynyl group, a 3-hexynyl group, and a 2-dodecynyl group).

Aliphatic hydrocarbon groups include substituted aliphatic hydrocarbon groups. Examples of the substituent that may substitute aliphatic hydrocarbon groups include halogen atoms, an epoxy group, a glycidyl group, a glycidoxy group, a mercapto group, a methacryloyl group, and an acryloyl group.

The aromatic hydrocarbon group represented by $R^1$ preferably has 6 or more and 20 or less carbon atoms, more preferably has 6 or more and 18 or less carbon atoms, still more preferably has 6 or more and 12 or less carbon atoms, and yet still more preferably has 6 or more and 10 or less carbon atoms.

Examples of the aromatic hydrocarbon group include a phenylene group, a biphenylene group, a terphenylene group, a naphthalene group, and an anthracene group.

Aromatic hydrocarbon groups include substituted aromatic hydrocarbon groups. Examples of the substituent that may substitute aromatic hydrocarbon groups include halogen atoms, an epoxy group, a glycidyl group, a glycidoxy group, a mercapto group, a methacryloyl group, and an acryloyl group.

Examples of the halogen atom represented by $R^2$ include a fluorine atom, a chlorine atom, a bromine atom, and an iodine atom. The halogen atom is preferably a chlorine atom, a bromine atom, or an iodine atom.

Examples of the alkoxy group represented by $R^2$ include alkoxy groups having 1 or more and 10 or less carbon atoms (preferably 1 or more and 8 or less carbon atoms, and more preferably 3 or more and 8 or less carbon atoms). Examples of the alkoxy group include a methoxy group, an ethoxy group, an isopropoxy group, a t-butoxy group, an n-butoxy group, an n-hexyloxy group, a 2-ethylhexyloxy group, and a 3,5,5-trimethylhexyloxy group. Alkoxy groups include substituted alkoxy groups. Examples of the substituent that may substitute alkoxy groups include halogen atoms, a hydroxyl group, amino groups, alkoxy groups, amide groups, and carbonyl groups.

The compound represented by formula (1) of $R^1{}_n SiR^2{}_m$, is preferably a compound where $R^1$ is a saturated aliphatic hydrocarbon group, in order to exhibit a high photocatalytic function and improve dispersibility. In particular, the compound represented by formula (1) of $R^1{}_n SiR^2{}_m$, is more preferably a compound where $R^1$ is a saturated aliphatic hydrocarbon group having 1 or more and 20 or less carbon atoms, $R^2$ is a halogen atom or an alkoxy group, n is an integer of 1 or more and 3 or less, and m is an integer of 1 or more and 3 or less, wherein n+m=4.

Examples of the compound represented by formula (1) of $R^1{}_n SiR^2{}_m$, include silane compounds, such as vinyltrimethoxysilane, methyltrimethoxysilane, ethyltrimethoxysilane, propyltrimethoxysilane, butyltrimethoxysilane, hexyltrimethoxysilane, n-octyltrimethoxysilane, decyltrimethoxysilane, dodecyltrimethoxysilane, vinyltriethoxysilane, methyltriethoxysilane, ethyltriethoxysilane, butyltriethoxysilane, hexyltriethoxysilane, decyltriethoxysilane, dodecyltriethoxysilane, phenyltrimethoxysilane, o-methylphenyltrimethoxysilane, p-methylphenyltrimethoxysilane, phenyltriethoxysilane, benzyltriethoxysilane, decyltrichlorosilane, and phenyltrichlorosilane (compounds where n=1 and m=3);

dimethyldimethoxysilane, dimethyldiethoxysilane, methylvinyldimethoxysilane, methylvinyldiethoxysilane, diphenyldimethoxysilane, diphenyldiethoxysilane, dimethyldichlorosilane, and dichlorodiphenylsilane (compounds where n=2 and m=2);

trimethylmethoxysilane, trimethylethoxysilane, trimethylchlorosilane, decyldimethylchlorosilane, triphenylchlorosilane (compounds where n=3 and m=1); and 3-glycidoxypropyltrimethoxysilane, γ-methacryloxypropyltrimethoxysilane, γ-mercaptopropyltrimethoxysilane, γ-chloropropyltrimethoxysilane, γ-aminopropyltrimethoxysilane, γ-aminopropyltriethoxysilane, γ-(2-aminoethyl) aminopropyltrimethoxysilane, γ-(2-aminoethyl)aminopropylmethyldimethoxysilane, γ-glycidyloxypropylmethyldimethoxysilane (compounds where $R^1$ is a substituted aliphatic hydrocarbon group or a substituted aromatic hydrocarbon group). The silane compound may be used alone or in combination of two or more.

To exhibit a high photocatalytic function and improve dispersibility, the hydrocarbon group in the silane compound represented by formula (1) is preferably an aliphatic hydrocarbon group, more preferably a saturated aliphatic hydrocarbon group, and still more preferably an alkyl group. To exhibit a high photocatalytic function and improve dispersibility, the hydrocarbon group in the silane compound is preferably a saturated aliphatic hydrocarbon group having 1 or more and 20 or less carbon atoms, more preferably a saturated aliphatic hydrocarbon group having 1 or more and 18 or less carbon atoms, still more preferably a saturated aliphatic hydrocarbon group having 4 or more and 12 or less carbon atoms, and yet still more preferably a saturated aliphatic hydrocarbon group having 4 or more and 10 or less carbon atoms.

Examples of organometallic compounds where the metal atom is aluminum include alkyl aluminates, such as triethoxyaluminum, tri-i-propoxyaluminum, and tri-sec-butoxyaluminum; aluminum chelates, such as di-i-propoxy. mono-sec-butoxyaluminum and di-i-propoxyaluminum. ethylacetoacetate; and aluminate coupling agents, such as acetoalkoxyaluminum diisopropylate.

Examples of organometallic compounds where the metal atom is titanium include titanate coupling agents, such as isopropyl triisostearoyl titanate, tetraoctyl bis(ditridecylphosphite)titanate, and bis(dioctylpyrophosphate)oxyacetate titanate; and titanium chelates, such as di-i-propoxy bis(ethylacetoacetate)titanium, di-i-propoxy bis(acetylacetonate)titanium, di-i-propoxy bis(triethanolaminate)titanium, di-i-propoxy titanium diacetate, and di-i-propoxy titanium dipropionate.

The organometallic compound may be used alone or in combination of two or more.

Method for Producing Photocatalyst Particles

The method for producing the photocatalyst particles is not limited. For example, the photocatalyst particles are produced by treating the surfaces of untreated particles with an organometallic compound.

An exemplary embodiment of the method for producing the photocatalyst particles will be described below.

The method for producing the photocatalyst particles may include, for example, (a) a step of treating the surfaces of untreated particles with an organometallic compound, and (b) a step of heating the particles during or after the step of treating the surfaces of untreated particles.

(a) Surface Treatment Step

Examples of the method for treating the surfaces of untreated particles with an organometallic compound include, but are not limited to, a method of bringing the organometallic compound itself into direct contact with the untreated particles; and a method of bringing a treatment solution, which is prepared by dissolving the organometallic compound in a solvent, into contact with the untreated particles. Specific examples include a method of adding, under stirring, the organometallic compound itself or the treatment solution to a dispersion prepared by dispersing the untreated particles in a solvent; and a method of adding (e.g., by dropping or spraying) the organometallic compound itself or the treatment solution to the untreated particles in the state of being fluidized, for example, by stirring with a HENSCHEL mixer or the like. In these methods, a reactive group (e.g., a hydrolyzable group, such as a halogen group or an alkoxy group) in the organometallic compound reacts with a hydroxyl group on the surfaces of the untreated particles, and the untreated particles undergo surface treatment accordingly.

The surface treatment step can be performed in the air or a nitrogen atmosphere. In the case of treating the surfaces of titanium oxide aerogel particles or silica-titania composite aerogel particles, which are used as untreated particles, the surface treatment step may be performed in supercritical carbon dioxide. In this process, the organometallic compound reaches deep into the pores of the porous particles, and the surface treatment is achieved deeply into the pores of the porous particles. The surface treatment may thus be performed in supercritical carbon dioxide.

The surface treatment step performed in supercritical carbon dioxide involves, for example, mixing an organometallic compound and a porous body in supercritical carbon dioxide under stirring to cause them to react with each other. Alternatively, the surface treatment step involves, for example, preparing a treatment solution by mixing an organometallic compound and a solvent, and mixing a porous body and the treatment solution in supercritical carbon dioxide under stirring. To maintain the pore structure of the porous body and increase the specific surface area, the organometallic compound may be placed in supercritical carbon dioxide after completion of the solvent removing step, causing the reaction of the organometallic compound with the surface of the porous body in supercritical carbon dioxide.

Examples of the solvent used to dissolve the organometallic compound include organic solvents (e.g., hydrocarbon solvents, ester solvents, ether solvents, halogenated solvents, alcohol solvents), water, and mixed solvents thereof. Examples of hydrocarbon solvents include toluene, benzene, xylene, hexane, octane, hexadecane, and cyclohexane. Examples of ester solvents include methyl acetate, ethyl acetate, isopropyl acetate, and amyl acetate. Examples of ester solvents include dibutyl ether and dibenzyl ether. Examples of halogenated solvents include 1,1-dichloro-1-fluoroethane, 1,1-dichloro-2,2,2-trifluoroethane, 1,1-dichloro-2,2,3,3,3-pentafluoropropane, chloroform, dichloroethane, and carbon tetrachloride. Examples of alcohol solvents include methanol, ethanol, and i-propyl alcohol. Examples of water include tap water, distilled water, and pure water. In addition to these solvents, solvents, such as dimethylformamide, dimethylacetamide, dimethyl sulfoxide, acetic acid, and sulfuric acid, may be used.

In the treatment solution prepared by dissolving the organometallic compound in the solvent, the concentration of the organometallic compound is preferably 0.05 mol/L or more and 500 mol/L or less, and more preferably 0.5 mol/L or more and 10 mol/L or less.

To exhibit a high photocatalytic function and improve dispersibility, the conditions for the surface treatment of the particles with the organometallic compound may be as follows. The surfaces of the untreated particles may be treated with 10 mass % or more and 100 mass % or less (preferably 20 mass % or more and 75 mass % or less, more preferably 25 mass % or more and 50 mass % or less) of the organometallic compound relative to the untreated particles. When the amount of the organometallic compound is 10 mass % or more, a high photocatalytic function tends to be exhibited even in the visible light region, and the dispersibility tends to be high. When the amount of the organometallic compound is 100 mass % or less, an excessive amount of the metal derived from the organometallic compound is unlikely to be present on the surfaces of the particles, and the deterioration of the photocatalytic function due to an excessive amount of the metal is unlikely to occur.

The temperature of the surface treatment of the untreated particles with the organometallic compound is preferably 15° C. or higher and 150° C. or lower, and more preferably 20° C. or higher and 100° C. or lower. The time of the surface treatment is preferably 10 minutes or longer and 120 minutes or shorter, and more preferably 30 minutes or longer and 90 minutes or shorter.

In the case of the surface treatment in supercritical carbon dioxide, the temperature and the pressure in the surface treatment step are the temperature and the pressure at which carbon dioxide is converted into the supercritical state. For example, the surface treatment step is performed in an atmosphere at a temperature of 50° C. or higher and 200° C. or lower and at a pressure of 10 MPa or higher and 30 MPa or lower. The reaction time is preferably 10 minutes or longer and 24 hours or shorter, more preferably 20 minutes or longer and 120 minutes or shorter, and still more preferably 30 minutes or longer and 90 minutes or shorter.

After the surface treatment of the untreated particles with the organometallic compound, a drying treatment may be performed. The drying treatment is not limited to any particular method and performed by a known drying method, such as a vacuum-drying method or a spray-drying method. The drying temperature may be 20° C. or higher and 150° C. or lower.

In the case of the surface treatment in supercritical carbon dioxide, a step of removing the solvent from the dispersion containing porous particles by using supercritical carbon dioxide is preferred, and a step of removing the solvent by circulating supercritical carbon dioxide in the dispersion after completion of the surface treatment step is more preferred.

(b) Heat Treatment Step

A heat treatment is performed during the step of treating the surfaces of the untreated particles or after the step of treating the surfaces of the untreated particles.

A heat treatment can be performed during the surface treatment of the untreated particles with the organometallic compound; during the drying treatment after the surface treatment; or separately after the drying treatment. To cause a sufficient reaction between the particles and the organometallic compound before the heat treatment, the heat treatment is preferably performed during the drying treatment after the surface treatment, or separately after the drying treatment. To appropriately perform the drying treatment, the heat treatment is more preferably performed separately after the drying treatment.

To exhibit a high photocatalytic function and improve dispersibility, the temperature of the heat treatment is preferably 180° C. or higher and 500° C. or lower, more preferably 200° C. or higher and 450° C. or lower, and still more preferably 250° C. or higher and 400° C. or lower. To exhibit a high photocatalytic function and improve dispersibility, the time of the heat treatment is preferably 10 minutes or longer and 300 minutes or shorter, and more preferably 30 minutes or longer and 120 minutes or shorter. When the heat treatment is performed during the step of treating the surfaces of the untreated particles, the heat treatment may be performed at the above-described heat treatment temperature after the organometallic compound is caused to sufficiently react with the particles at the above-described surface treatment temperature. When the heat treatment is performed in the drying treatment after the surface treatment, the temperature of the drying treatment corresponds to the temperature of the heat treatment.

When the temperature of the heat treatment is 180° C. or higher and 500° C. or lower, particles that exhibit a high photocatalytic function even in the visible light region are obtained efficiently. The heat treatment at 180° C. or higher and 500° C. or lower may appropriately oxidize the hydrocarbon group derived from the metal compound present on the surfaces of the particles and may change some of C—C bonds or C=C bonds into C—O bonds or C=O bonds.

The heat treatment may be performed in an atmosphere with an oxygen concentration (volume %) of 1% or more and 21% or less. The heat treatment in this oxygen atmosphere can appropriately and efficiently oxidize the hydrocarbon group derived from the metal compound present on the surfaces of the particles. The oxygen concentration (volume %) is more preferably 3% or more and 21% or less and still more preferably 5% or more and 21% or less.

Examples of the method for the heat treatment include, but are not limited to, known heating methods, such as heating in an electric furnace, a firing furnace (e.g., Roller hearth kiln, Shuttle kiln), and a radiation heating furnace; and heating with a laser beam, infrared rays, UV rays, a microwave, and the like.

The photocatalyst particles are appropriately produced through the above-described steps.

Characteristics of Photocatalyst Particles

The photocatalyst particles have absorption at wavelengths of 450 nm and 750 nm in the visible absorption spectrum.

In order that the photocatalyst particles exhibit a high photocatalytic function even in the visible light region, the photocatalyst particles preferably have absorption at wavelengths of 450 nm, 600 nm, and 750 nm in the visible absorption spectrum, more preferably have absorption in the entire wavelength range of 450 nm or more and 750 nm or less in the visible absorption spectrum, and still more preferably have absorption in the entire wavelength range of 400 nm or more and 800 nm or less in the visible absorption spectrum.

In order that the photocatalyst particles exhibit a high photocatalytic function even in the visible light region, assuming that the absorbance at a wavelength of 350 nm is 1, the absorbance at a wavelength of 450 nm is 0.02 or more, preferably 0.1 or more, more preferably 0.2 or more, and still more preferably 0.3 or more, the absorbance at a wavelength of 600 nm is 0.02 or more, preferably 0.1 or more, and more preferably 0.2 or more, and the absorbance at a wavelength of 750 nm is 0.02 or more, preferably 0.05 or more, and more preferably 0.1 or more, in the ultraviolet-visible absorption spectrum.

The ultraviolet-visible absorption spectrum of the photocatalyst particles is obtained by the following method. The particles targeted for measurement are dispersed in tetrahydrofuran, and the dispersion is then applied to a glass substrate and dried at 24° C. in the air. Using a spectrophotometer (e.g., U-4100 available from Hitachi High-Technologies Corporation, scanning speed: 600 nm, slit width: 2 nm, sampling interval: 1 nm), a diffuse reflectance spectrum in the wavelength range from 200 nm to 900 nm is measured in a diffuse reflectance configuration. From the diffuse reflectance spectrum, the absorbance at given wavelengths is theoretically determined by Kubelka-Munk conversion to obtain an ultraviolet-visible absorption spectrum.

The photocatalyst particles may have an absorption peak in the wavenumber range of 2700 $cm^{-1}$ or more and 3000 $cm^{-1}$ or less in the infrared absorption spectrum.

Specifically, for example, the photocatalyst particles may have at least one absorption peak in the wavenumber range of 2700 $cm^{-1}$ or more and 3000 $cm^{-1}$ or less in the infrared absorption spectrum. The expression "having an absorption peak" means having absorption with an absorption intensity (absorbance) of 0.022 (transmittance 5%) or more.

The infrared absorption spectrum of the photocatalyst particles is measured by the following method. First, titanium oxide particles targeted for measurement are prepared as a test sample by using the KBr pellet method. The infrared absorption spectrum of the test sample in the wavenumber range of 500 $cm^{-1}$ or more and 4,000 $cm^{-1}$ or less is then determined with an infrared spectrophotometer (FT-IR-410 available from JASCO Corporation) under the conditions of an integration number of 300 times and a resolution of 4 $cm^{-1}$.

The average particle size of the photocatalyst particles is preferably 0.01 μm or more and 0.5 μm or less, more preferably 0.02 μm or more and 0.15 μm or less, and still more preferably 0.02 μm or more and 0.1 μm or less. When the average particle size of the photocatalyst particles is 0.01 μm or more, the particles are unlikely to aggregate, and the photocatalyst particles thus tend to have a high photocatalytic function. When the average particle size of the photocatalyst particles is 0.5 μm or less, the ratio of the specific surface area to the amount is large, and the photocatalyst particles tend to have a high photocatalytic function. When the average particle size of the photocatalyst particles is in the above-described range, the photocatalyst particles tend to exhibit a high photocatalytic function in the visible light region.

The average particle size of the photocatalyst particles refers to, when the photocatalyst particles are aerogel particles, the average particle size of the primary particles forming the aerogel particles.

The average particle size of the photocatalyst particles is the average particle size of the primary particles (average primary particle size) and is measured as described below.

While the photocatalyst particles are attached to the resin particles, the image of the photocatalyst particles is captured by observation under a scanning electron microscope (S-4100 available from Hitachi, Ltd.). In this case, the image is captured with the scanning electron microscope at a magnification adjusted so as to perform image analysis on plural primary particles. The captured image is loaded into an image analyzer (LUZEXIII available from Nireco Corporation). The area of each particle is determined by image analysis of the primary particles, and the equivalent circular diameter (μm) is calculated from the area. The mean of the equivalent circular diameter is taken as an average primary particle size (μm). The average primary particle size is determined by analyzing about 10 to 50 primary particles.

When the photocatalyst particles are silica-titania composite aerogel particles, the photocatalyst particles may be particles formed by treating, with the organometallic compound, the surfaces of untreated silica-titania composite aerogel particles having a titania layer in its surface layer.

Specifically, these particles include base particles (e.g., base particles having an elemental ratio Si/Ti of silicon to titanium of more than 0 and 6 or less), a titania layer (hereinafter also referred to as an "intermediate layer") present on the surface of the base particles, and a layer formed, on the surface of the titania layer, by bonding a metal compound having a metal atom and a hydrocarbon group to the surface via an oxygen atom (i.e., a layer containing a metal compound having a metal atom and a hydrocarbon group, hereinafter also referred to as a "surface layer").

The following method confirms that the silica-titania composite aerogel particles have the above-described layers. The following method also confirms that particles other than the silica-titania composite aerogel particles have a surface layer.

The XPS qualitative analysis (wide scan analysis) is performed by etching the silica-titania composite aerogel particles with a rare gas ion in the depth direction from the surface to identify and quantitatively determine at least titanium, silicon, and carbon. From the obtained data, the elemental profiles where the vertical axis indicates peak intensity and the horizontal axis indicates etching time are drawn for at least titanium, silicon, and carbon. Each profile curve is divided into plural regions at inflection points, and the following regions are specified: a region that reflects the elemental composition of the base particles, a region that reflects the elemental composition of the intermediate layer, and a region that reflects the elemental composition of the surface layer. When the elemental profiles include a region that reflects the elemental composition of the intermediate layer, the silica-titania composite aerogel particles are determined to have the intermediate layer. When the elemental profiles include a region that reflects the elemental composition of the surface layer, the silica-titania composite aerogel particles are determined to have the surface layer.

The elemental profiles will be described below with reference to FIG. 6.

Figure 6:
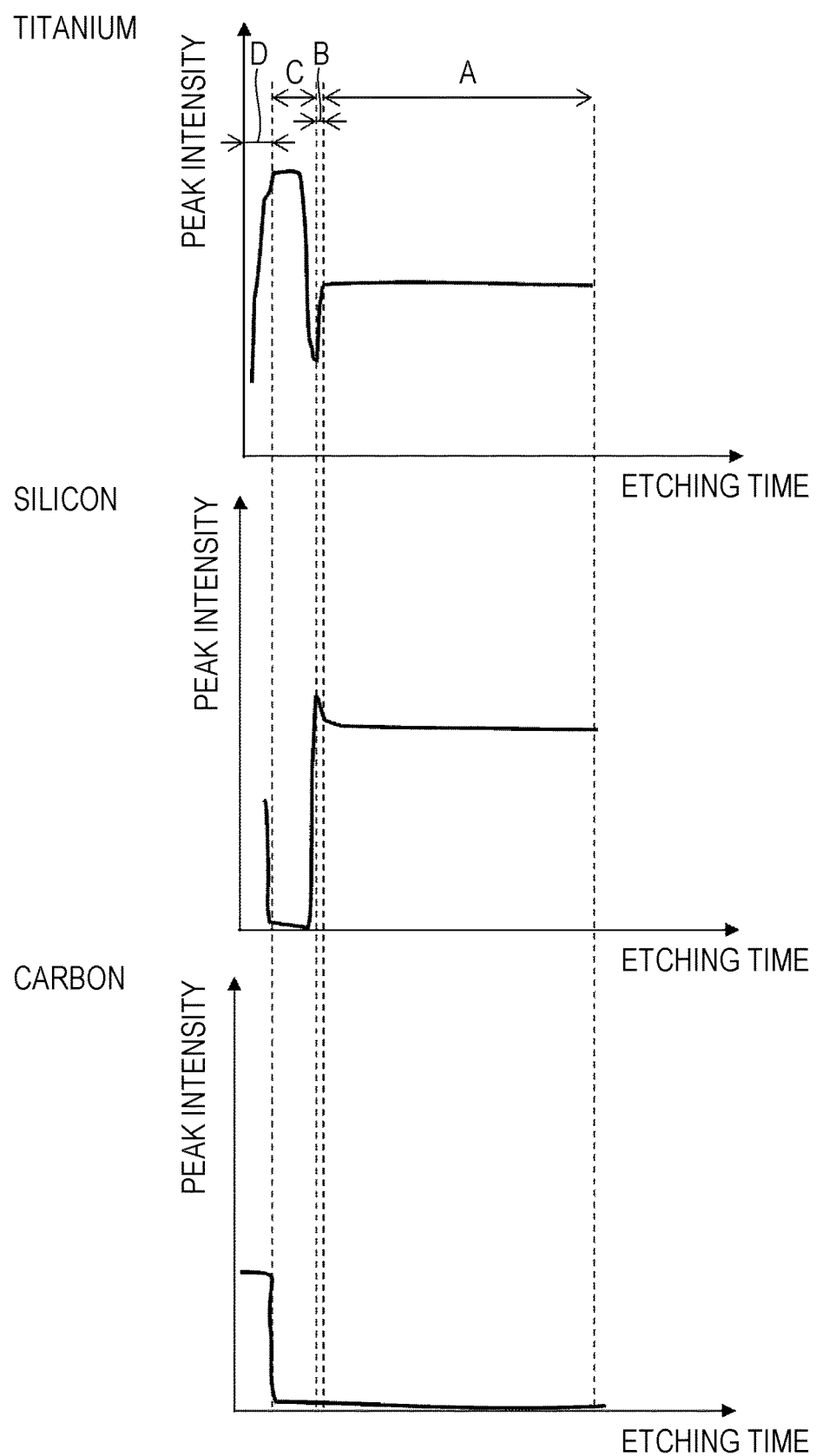
FIG. 6 illustrates examples of the elemental profiles of silica-titania composite particles and includes, in sequence from top, an elemental profile for titanium, an elemental profile for silicon, and an elemental profile for carbon.

FIG. 6 illustrates examples of the elemental profiles of the silica-titania composite aerogel particles and includes, in sequence from top, an elemental profile for titanium, an elemental profile for silicon, and an elemental profile for carbon.

The elemental profiles illustrated in FIG. 6 are divided into a region A, a region B, a region C, a region D at the inflection points of the profile curve.

Region A: a region that is present at the final stage of etching and in which the titanium peak intensity and the silicon peak intensity are substantially constant.

Region B: a region that is present immediately before the region A and in which the closer to the surface of the particles, the lower the titanium peak intensity and the higher the silicon peak intensity.

Region C: a region that is present immediately before the region B and in which the titanium peak intensity is substantially constant and silicon is rarely detected.

Region D: a region that is present at the initial stage of etching and in which the carbon peak intensity is substantially constant and a metal element is also detected.

The region A and the region B are regions that reflect the elemental composition of the base particles. In the production of the base particles, the base particles are formed by forming covalent bonds between silica and titania at the ratio corresponding to the mixing ratio of the alkoxy silane and the titanium alkoxide, which are materials of the silica-titania composite. However, silica is more likely to appear on the surface of the base particles than titania. As a result, the elemental profiles include the region A that is present at the final stage of etching and in which the titanium peak intensity and the silicon peak intensity are substantially constant; and the region B that is present immediately before the region A and in which the closer to the surface of the particles, the lower the titanium peak intensity and the higher the silicon peak intensity.

The region C is a region that reflects the elemental composition of the intermediate layer. When the region C, which is a region in which the titanium peak intensity is substantially constant and silicon is rarely detected, is present immediately before the region B, the silica-titania composite aerogel particles are determined to have an intermediate layer, which is a "titania layer".

The region C reflects the elemental composition of a first layer, but does not necessarily completely correspond to the intermediate layer. A portion of the region C adjacent to the region B may reflect the elemental composition of the base particles.

The region D is a region that reflects the elemental composition of the surface layer. When the region D, which is a region in which the carbon peak intensity is substantially constant and a metal element is also detected, is present at the initial stage of etching, the silica-titania composite aerogel particles are determined to have a surface layer, which is a "layer containing a metal compound having a metal atom and a hydrocarbon group".

Since silicon, aluminum, and titanium are candidates for the metal atom of the metal compound in the surface layer, the identification and quantitative determination of aluminum are also performed by XPS as needed, and the elemental profile for aluminum is also drawn.

The region D reflects the elemental composition of the surface layer, but does not necessarily completely correspond to a second layer. A portion of the region D adjacent to the region C may reflect the elemental composition of the first layer.

The elemental profiles illustrated in FIG. 6 indicate that the silica-titania composite aerogel particles have base particles, an intermediate layer, and a surface layer, and the metal atom of the metal compound in the surface layer is silicon.

Resin Particles

Examples of the resin particles include fluorocarbon-based resin particles, silicone-based resin particles, polyester-based resin particles, (meth)acrylic-based resin particles, styrene-based resin particles, acrylonitrile/styrene copolymer resin particles, acrylonitrile/butadiene/styrene copolymer (ABS) resin particles, epoxy-based resin particles, polycarbonate-based resin particles, polyamide-based resin particles, polyamine-based resin particles, urethane-based resin particles, polyether-based resin particles, polysulfide-based resin particles, polyphenol-based resin particles, vinyl chloride-based resin particles, and olefin-based resin particles, particles of complexes thereof, and silicone-modified or halogen-modified resin particles thereof.

In view of the adhesion and dispersibility of the photocatalyst particles, silicone-based resin particles, (meth) acrylic-based resin particles, and styrene-based resin particles are preferred among these particles. To suppress embedding of the photocatalyst particles and suppress decomposition and deterioration of the resin particles caused by the photocatalyst particles, silicone-based resin particles, crosslinked acrylic-based resin particles, and crosslinked styrene-based resin particles are more preferred, and silicone-based resin particles are still more preferred.

The term "based" for each resin means that the resin may be a copolymer resin with other resins and also means that the corresponding resin component is contained at the highest molar ratio among other resin components. In other words, silicone-based resins include, in addition to a homopolymer resin composed of a silicone resin component, copolymer resins that are copolymer resins with other resin components and each contain a silicone resin component in the greatest proportion among the other resin components.

Here, the silicone-based resin particles are particles containing a polysiloxane component as a main component (the greatest proportion of component among all components). The molecular structure of silicone may have a straight chain, a branched chain, or a mixture of these. Examples of the organic group bonded to the silicon atom include alkyl groups, such as a methyl group, an ethyl group, and a propyl group; aryl groups, such as a phenyl group and a tolyl group; and alkyl halide groups, such as a chloromethyl group.

Specific examples of the silicone-based resin particles include particle-like crosslinked dimethylpolysiloxane, and polysilsesquioxane and derivatives thereof. In view of the adhesion and dispersibility of the photocatalyst particles, the silicone-based resin particles are preferably monodisperse silicone resin particles with narrow particle size distribution.

Examples of commercial products of the silicone-based resin particles include silicone resin powders KMP-701 and X-52-1621 available from Shin-Etsu Chemical Co., Ltd.; and silicone rubber powders KMP-597, KMP-598, X-52-875, and KMP-601 available from Shin-Etsu Chemical Co., Ltd.

The silicone-based resin particles may be what are called rubber particles.

Examples of the (meth)acrylic-based resin particles include poly(meth)acrylate particles including 50 mass % or more (preferably 70 mass % or more, more preferably 90 mass %, and still more preferably 100 mass %) of a structural unit derived from a (meth)acrylic acid alkyl ester.

Examples of the (meth)acrylic acid alkyl ester include (meth)acrylic acid alkyl esters having an alkyl chain with 1 or more and 8 or less carbon atoms (preferably 1 or more and 4 or less carbon atoms, more preferably 1 or more and 2 or less carbon atoms, and still more preferably 1 carbon atom).

In view of the adhesion and dispersibility of the photocatalyst particles, the (meth)acrylic-based resin particles are preferably monodisperse poly(methyl methacrylate) particles (PMMA particles) with narrow particle size distribution. To suppress embedding of the photocatalyst particles and suppress decomposition and deterioration of the resin particles caused by the photocatalyst particles, crosslinked poly(methyl methacrylate) particles (crosslinked PMMA particles) are more preferred.

Examples of commercial products of the (meth)acrylic-based resin particles include MX-1000, MZ-SHN, and MZ-20HN available from Soken Chemical & Engineering Co., Ltd.

In view of the adhesion and dispersibility of the photocatalyst particles and to suppress decomposition and deterioration of the resin particles caused by the photocatalyst particles, the styrene-based resin particles are preferably monodisperse crosslinked styrene resin particles with narrow particle size distribution.

Examples of commercial products of the styrene-based resin particles include SX-350H and SX-500H available from Soken Chemical & Engineering Co., Ltd.

In view of the adhesion and dispersibility of the photocatalyst particles, to prevent or reduce the detachment of the photocatalyst particles from the holding member, and to improve the air permeability, liquid permeability, and deodorizing performance of the filter, the average particle size of the resin particles is preferably 0.5 μm or more and 50 μm or less, more preferably 3 μm or more and 20 μm or less, and still more preferably 5 μm or more and 15 μm or less.

Characteristics of Photocatalyst-Attached Resin Particles

In view of the adhesion and dispersibility of the photocatalyst particles and to improve the deodorizing performance of the filter, the ratio (photocatalyst particles/resin particles) of the average particle size of the photocatalyst particles to the average particle size of the resin particles in the photocatalyst-attached resin particles is preferably 0.001 or more and 0.1 or less, more preferably 0.002 or more and 0.05 or less, and still more preferably 0.003 or more and 0.03 or less.

The average particle size of the resin particles corresponds to the average particle size of the primary particles (average primary particle size) and is measured as described below.

The photocatalyst particles attached to the resin particles are removed by ultrasonication or the like. It is noted that the photocatalyst particles are not necessarily completely removed.

The image of the resin particles after the photocatalyst particles are removed is captured by observation under a scanning electron microscope (S-4100 available from Hitachi, Ltd.). In this case, the image is captured with the scanning electron microscope at a magnification adjusted so as to perform image analysis on plural primary particles. The captured image is loaded into an image analyzer (LUZEXIII available from Nireco Corporation). The area of each particle is determined by image analysis of the primary particles, and the equivalent circular diameter (μm) is calculated from the area. The mean of the equivalent circular diameter is taken as an average primary particle size (μm). The average primary particle size is determined by analyzing about 10 to 50 primary particles.

To improve the deodorizing performance of the filter, the coverage of the photocatalyst particles on the resin particles in the photocatalyst-attached resin particles is preferably 30% or more and 100% or less, more preferably 50% or more and 100% or less, and still more preferably 70% or more and 100% or less.

The coverage of the photocatalyst particles on the resin particles is measured as described below.

The image of the resin particles having the photocatalyst particles is captured by observation under a scanning electron microscope (S-4100 available from Hitachi, Ltd.). In this case, the image is captured with the scanning electron microscope at a magnification adjusted so as to perform image analysis on plural resin particles having the photocatalyst particles. The captured image is loaded into an image analyzer (LUZEXIII available from Nireco Corporation). The area ratio of parts of the resin particle surface with the photocatalyst particles is calculated. The coverage is obtained by analyzing about 10 to 50 resin particles having the photocatalyst particles.

Specifically, the coverage of the photocatalyst particles covering the resin particles are obtained in accordance with the following formula, and the mean of the coverage is taken as the coverage of the photocatalyst particles.

Coverage (%) of photocatalyst particles=(area of parts with photocatalyst particles)/(area of resin particles)×100

To prevent or reduce the detachment of the photocatalyst particles from the filter due to an impact or the like, the proportion of the photocatalyst particles released from the resin particles in the photocatalyst-attached resin particles is preferably 1% or more and 50% or less, more preferably 3% or more and 40% or less, and still more preferably 5% or more and 30% or less.

When the proportion of the released photocatalyst particles is 1% or more, the deterioration of the photocatalytic effect (i.e., the deterioration of the deodorizing performance of the filter) caused as a result of embedding of the photocatalyst particles in the resin particle surface with an excessively strong force is unlikely to occur.

When the proportion of the released photocatalyst particles is 50% or less, the detachment of the photocatalyst particles from the holding member is prevented or reduced.

The proportion of the released photocatalyst particles is controlled by the particle size of the resin particles and the particle size of the photocatalyst particles and the conditions (e.g., the number of rotations of a mixer) for attaching the photocatalyst particles to the resin particles.

The proportion of the photocatalyst particles released from the resin particles is determined as described below.

A dispersion is prepared by dispersing 2 g of the resin particles having the photocatalyst particles in 40 ml of a 0.2% aqueous solution of a surfactant (polyoxyethylene octylphenyl ether (available from Wako Pure Chemical Industries, Ltd.)). The photocatalyst particles are released from the resin particle surface by applying ultrasonic vibration (output 20 W, frequency 20 kHz) to the dispersion for 1 minute. The supernatant of the dispersion is then removed, and pure water is added, followed by filtering and drying. As a result, the resin particles from which the photocatalyst particles have been released are obtained.

The amount of an "atom (e.g., titanium atom) in the photocatalyst particles" of the resin particles having the photocatalyst particles before ultrasonic vibration, and the amount of the "atom (e.g., titanium atom) in the photocatalyst particles" of the resin particles that are obtained after ultrasonic vibration and from which the photocatalyst particles have been released are measured with fluorescent X-rays, and the proportion of the photocatalyst particles released from the resin particles is calculated in accordance with the following formula.

> Proportion (%) of photocatalyst particles released from resin particles=((amount of "atom (e.g., titanium atom) in photocatalyst particles" of resin particles before ultrasonic vibration)–(amount of "atom (e.g., titanium atom) in photocatalyst particles" of resin particles after ultrasonic vibration))/(amount of "atom (e.g., titanium atom) in photocatalyst particles" of resin particles before ultrasonic vibration)×100

To improve the deodorizing performance of the filter, the combination of the resin particles and the photocatalyst particles is preferably a combination in which the resin particles are at least one type of particles selected from silicone-based resin particles, crosslinked styrene-based resin particles, and crosslinked acrylic-based resin particles (preferably, crosslinked poly(methyl methacrylate) resin particles), and the photocatalyst particles are metatitanic acid particles, and more preferably a combination in which the resin particles are silicone-based resin particles and the photocatalyst particles are metatitanic acid particles.

Method for Producing Photocatalyst-Attached Resin Particles

Examples of the method for producing the photocatalyst-attached resin particles include, but are not limited to, a method of adding the photocatalyst particles to the resin particles and mixing these particles. Examples of the mixer used include a V-blender, a HENSCHEL mixer, and a Lodige mixer.

Coarse particles of the photocatalyst-attached resin particles may be removed with, for example, a vibration screening machine, a wind-power screening machine, as needed.

Characteristics of Filter

In view of filter function, the air permeability of the filter according to the exemplary embodiment is preferably 1 ($cm^3/cm^2 \cdot sec$) or more and 300 ($cm^3/cm^2 \cdot sec$) or less, and more preferably 5 ($cm^3/cm^2 \cdot sec$) or more and 200 ($cm^3/cm^2 \cdot sec$) or less.

The air permeability of the filter is measured as described below.

The air permeability of the filter is measured with a frazir-type air permeability tester AP-360SM (available from Daiei Kagaku Seiki Mfg. Co., Ltd.). Specifically, a test piece, about 20 cm×20 cm, is attached to an end of the cylinder in the frazir-type air permeability tester, and then a suction fan is controlled with a rheostat so that the inclined manometer shows a pressure of 125 Pa (1.27 $cmH_2O$). On the basis of the pressure shown by the vertical manometer and the type of vent hole used in this case, the amount ($cm^3/cm^2/s$) of air passing through the test piece is obtained from the table attached the tester. The measurement is performed 5 times, and the mean is taken as the air permeability of the filter.

The filter according to the exemplary embodiment may have visible light transmissivity. This is because the photocatalyst particles having a high photocatalytic function in the visible light region efficiently exhibit a catalytic function.

Specifically, the visible light transmittance of the filter is preferably 30% or more and more preferably 50% or more.

The visible light transmittance of the filter is measured as described below.

The total light transmittance (%) is measured by using a haze meter (NDH-2000 available from Nippon Denshoku Industries Co., Ltd,) in accordance with JIS K7361-1:1997.

EXAMPLES

Exemplary embodiments of the present disclosure will be described below in detail by way of Examples, but exemplary embodiments of the present disclosure are not limited by these Examples. In the following description, the unit "part" is on a mass basis, unless otherwise specified.

Preparation of Photocatalyst Particles

Metatitanic Acid Particles MTA1

To a titanyl sulfate solution in which the $TiO_2$ concentration is 260 g/L and the $Ti^{3+}$ concentration in terms of $TiO_2$ is 6.0 g/L, a separately prepared anatase seed is added in an amount of 8 mass % in terms of $TiO_2$ relative to $TiO_2$ in the titanyl sulfate solution. Next, this solution is heated at the boiling point or higher to hydrolyze titanyl sulfate ($TiOSO_4$) and thus to generate particle-like metatitanic acid. Next, the metatitanic acid particles are filtered and washed, and a slurry of the metatitanic acid particles is then prepared and subjected to neutralization and washing at pH 7. Accordingly, a metatitanic acid slurry with an average particle size of 0.042 μm is prepared.

Next, a 5 N aqueous solution of sodium hydroxide is added to the metatitanic acid slurry with an average particle size of 0.042 μm under stirring until the pH reaches 8.5. The slurry is maintained under stirring for 2 hours and then neutralized with 6 N hydrochloric acid until the pH reaches 5.8, followed by filtering and washing with water. After washing, water is added again to form a slurry again, and 6 N hydrochloric acid is added to the slurry under stirring until the pH reaches 1.3. The slurry is maintained under stirring for 3 hours. From the slurry, 100 parts by mass of metatitanic acid is separated. To 100 parts by mass of metatitanic acid, 30 parts by mass of hexyltrimethoxysilane is added under continuous heating at 60° C. and stirring. The mixture is stirred for 30 minutes and then neutralized to pH 7 by addition of a 7 N aqueous solution of sodium hydroxide, followed by filtering and washing with water. The residue after filtering and washing with water is spray-dried in a jet dryer at an outlet temperature of 150° C. to produce a dried powder. The obtained dried powder is heated at 280° C. for 90 minutes in an electric furnace with an oxygen concentration (volume %) of 12% to yield metatitanic acid particles MTA1.

Metatitanic Acid Particles MTA2

Metatitanic acid particles MTA2 with an average particle size of 0.095 μm are produced in the same manner as for the metatitanic acid particles MTA1 except that the amount of the anatase seed added is 6 mass %.

Metatitanic Acid Particles MTA3

Metatitanic acid particles MTA3 with an average particle size of 0.150 μm are produced in the same manner as for the metatitanic acid particles MTA1 except that the amount of the anatase seed added is 4 mass %.

Titanium Oxide Particles TO1

To a dispersion in which commercial anatase-type titanium oxide particles ("SSP-25 (available from Sakai Chemical Industry Co., Ltd.)", average particle size 0.010 μm) are dispersed in methanol, 35 mass % of hexyltrimethoxysilane relative to the untreated titanium oxide particles is added dropwise. The mixture is caused to react at 40° C. for 1 hour and then spray-dried at an outlet temperature of 120° C. to produce a dried powder. The obtained dried powder is heated at 290° C. for 1 hour in an electric furnace with an oxygen concentration (volume %) of 18% to yield titanium oxide particles TO1.

Titanium Oxide Particles TO2

To a dispersion in which commercial anatase-type titanium oxide particles ("ST-21 (available from Ishihara Sangyo Kaisha, Ltd.)", average particle size 0.020 μm) are dispersed in methanol, 30 mass % of octyltrimethoxysilane relative to the untreated titanium oxide particles is added dropwise. The mixture is caused to react at 40° C. for 1 hour and then spray-dried at an outlet temperature of 120° C. to produce a dried powder. The obtained dried powder is heated at 270° C. for 1 hour in an electric furnace with an oxygen concentration (volume %) of 20% to yield titanium oxide particles T02.

Titanium Oxide Particles TO3

To a dispersion that is prepared by a sol-gel method and in which anatase-type titanium oxide particles with an average particle size of 0.450 μm are dispersed in methanol, 25 mass % of hexyltrimethoxysilane relative to the untreated titanium oxide particles is added dropwise. The mixture is caused to react at 40° C. for 1 hour and then spray-dried at an outlet temperature of 120° C. to produce a dried powder. The obtained dried powder is heated at 300° C. for 1 hour in an electric furnace with an oxygen concentration (volume %) of 18% to yield titanium oxide particles T03.

Titanium Oxide Aerogel Particles TOAG1

To a reaction container, 115.4 parts of methanol and 14.3 parts of tetrabutoxy titanium are placed and mixed. While the mixture is stirred at 100 rpm with a magnetic stirrer, 7.5 parts of a 0.009 mass % aqueous solution of oxalic acid is added to the mixture over 30 seconds. The mixture is maintained under stirring for 30 minutes to form 137.3 parts of a dispersion (1) (solid content: 3.4 parts, liquid phase: 133.9 parts).

Next, 137.3 parts of the dispersion (1) is placed in a reaction vessel, and the temperature and pressure are increased to 150° C./20 MPa by introducing $CO_2$ to the reaction vessel with the dispersion (1) being stirred at 85 rpm. While the dispersion (1) is continuously stirred, $CO_2$ is caused to flow in and flow out, and 133 parts of the liquid phase is removed over 60 minutes.

Next, to the solid phase that remains after the liquid phase is removed, a mixture of 3.4 parts of isobutyltrimethoxysilane and 3.4 parts of methanol is added over 5 minutes. The resultant mixture is maintained at 150° C./20 MPa for 30 minutes under stirring at 85 rpm. While the mixture is continuously stirred, $CO_2$ is caused to flow in and flow out, and 6.5 parts of the liquid phase is removed over 30 minutes. The pressure is reduced to the atmospheric pressure over 30 minutes, and 4.6 parts of a powder is collected.

Next, 4.0 parts of the powder is measured out in a SUS container and heated at 315° C. for 60 minutes in an electric furnace with an oxygen concentration (volume %) of 20%. The powder is allowed to cool to 30° C. The obtained powder is filtered through a vibrating screen with a mesh size of 45 μm to remove coarse particles and, as a result, 3.5 parts of a powder (titanium oxide aerogel particles TOAG1) is collected.

Silica-Titania Composite Aerogel Particles STAG1

To a reaction container, 115.4 parts of methanol and 7.2 parts of tetramethoxysilane are placed and mixed. To the reaction container, 7.2 parts of tetrabutoxy titanium is further placed and mixed. While the mixture is stirred at 100 rpm with a magnetic stirrer, 7.5 parts of a 0.009 mass % aqueous solution of oxalic acid is added to the mixture over 30 seconds. The mixture is maintained under stirring for 30 minutes to form 137.2 parts of a first dispersion (I-1) (solid content: 4.5 parts, liquid phase: 132.7 parts).

Next, 137.2 parts of the first dispersion (I-1) is placed in a reaction container, and the temperature and pressure are increased to 150° C./20 MPa by introducing $CO_2$ to the reaction container with the first dispersion (I-1) being stirred at 85 rpm. While the first dispersion (I-1) is continuously stirred, $CO_2$ is caused to flow in and flow out, and 132.0 parts of the liquid phase is removed over 60 minutes.

Next, to the solid phase that remains after the liquid phase is removed, a mixture of 4.5 parts of isobutyltrimethoxysilane and 4.5 parts of methanol is added over 5 minutes. The resultant mixture is maintained at 150° C./20 MPa for 30 minutes under stirring at 85 rpm. While the mixture is continuously stirred, $CO_2$ is caused to flow in and flow out, and 8.2 parts of the liquid phase is removed over 30 minutes. The pressure is reduced to the atmospheric pressure over 30 minutes, and 6.0 parts of a powder is collected.

Next, 4.0 parts of the powder is measured out in a SUS container and placed on a hot plate. The powder is heated to 380° C., maintained for 60 minutes, and allowed to cool to 30° C. The obtained powder is filtered through a vibrating screen with a mesh size of 45 μm to remove coarse particles and, as a result, 3.5 parts of a powder (silica-titania composite aerogel particles STAG1) is collected.

The silica-titania composite aerogel particles STAG1 include base particles having an elemental ratio Si/Ti of silicon to titanium of 3.1, and a surface layer containing isobutyltrimethoxysilane present on the surface of the base particles.

Silica-Titania Composite Aerogel Particles STAG2

To a reaction container, 115.4 parts of methanol and 7.2 parts of tetramethoxysilane are placed and mixed. To the reaction container, 7.2 parts of tetrabutoxy titanium is further placed and mixed. While the mixture is stirred at 100 rpm with a magnetic stirrer, 7.5 parts of a 0.009 mass % aqueous solution of oxalic acid is added to the mixture over 30 seconds. The mixture is maintained under stirring for 30 minutes to form 137.2 parts of a first dispersion (I-1) (solid content: 4.5 parts, liquid phase: 132.7 parts).

Next, 137.2 parts of the first dispersion (I-1) is placed in a reaction container. While the first dispersion (I-1) is stirred at 100 rpm with a magnetic stirrer, a mixture of 1.5 parts of tetrabutoxy titanium and 4.5 parts of butanol is added dropwise over 10 minutes. The mixture is maintained under stirring for 30 minutes to form 143.2 parts of a second dispersion (II-1) (solid content: 5.0 parts, liquid phase: 138.2 parts).

Next, 143.2 parts of the second dispersion (II-1) is placed in a reaction vessel, and the temperature and pressure are increased to 150° C./20 MPa by introducing $CO_2$ to the reaction vessel with the second dispersion (II-1) being stirred at 85 rpm. While the second dispersion (II-1) is continuously stirred, $CO_2$ is caused to flow in and flow out, and 138 parts of the liquid phase is removed over 60 minutes.

Next, to the solid phase that remains after the liquid phase is removed, a mixture of 4.5 parts of isobutyltrimethoxysilane and 4.5 parts of methanol is added over 5 minutes. The resultant mixture is maintained at 150° C./20 MPa for 30 minutes under stirring at 85 rpm. While the mixture is continuously stirred, $CO_2$ is caused to flow in and flow out, and 7.0 parts of the liquid phase is removed over 30 minutes. The pressure is reduced to the atmospheric pressure over 30 minutes, and 7.2 parts of a powder is collected.

Next, 4.0 parts of the powder is measured out in a SUS container and placed on a hot plate. The powder is heated to 450° C., maintained for 60 minutes, and allowed to cool to 30° C. The obtained powder is filtered through a vibrating screen with a mesh size of 45 μm to remove coarse particles and, as a result, 3.5 parts of a powder (silica-titania composite aerogel particles STAG2) is collected.

The silica-titania composite aerogel particles STAG2 include base particles having an elemental ratio Si/Ti of silicon to titanium of 3.1, a titania layer (intermediate layer) present on the surface of the base particles, and a surface layer containing isobutyltrimethoxysilane present on the surface of the titania layer.

The following characteristics of the photocatalyst particles produced as described above are determined in accordance with the foregoing methods. The photocatalyst particles are listed in Table 1.

Visible Absorption Spectrum Characteristics (expressed as "Visi Characteristics" in Table: the absorbance at a wavelength of 450 nm, the absorbance at a wavelength of 600 nm, and the absorbance at a wavelength of 750 nm, assuming that the absorbance at a wavelength of 350 nm is 1), Infrared Absorption Spectrum Characteristics (expressed as "IR Characteristics" in Table: the presence or absence of absorption peaks in the wavenumber range of 2700 $cm^{-1}$ or more and 3,000 $cm^{-1}$ or less, and the wavenumber of the absorption peaks)

Average Particle Size (expressed as "Particle Size DC" in Table)

Production of Catalyst-Attached Resin Particles

The following resin particles are provided.

Silicone-based resin particles SR1 (trade name "KMP-598 (available from Shin-Etsu Chemical Co., Ltd.)", average particle size DR=13.5 μm)

Silicone-based resin particles SR2 (trade name "X-52-1621 (available from Shin-Etsu Chemical Co., Ltd.)", average particle size DR=5.0 μm)

Silicone-based resin particles SR3 (trade name "X-52-854 (available from Shin-Etsu Chemical Co., Ltd.)", average particle size DR=0.7 μm)

Crosslinked PMMA particles MMA1 (trade name "MX-1000 (available from Soken Chemical & Engineering Co., Ltd.)", average particle size DR=11.0 μm)

Crosslinked PMMA particles MMA2 (trade name "MZ-20HN (available from Soken Chemical & Engineering Co., Ltd.)", average particle size DR=18.5 μm)

Crosslinked styrene particles ST1 (trade name "SX-350H (available from Soken Chemical & Engineering Co., Ltd.)", average particle size DR=3.5 μm)

Crosslinked styrene particles ST2 (trade name "SGP-150C (available from Soken Chemical & Engineering Co., Ltd.), average particle size DR=49.5 μm)

The photocatalyst particles are added to the resin particles at the combination and the quantitative ratio shown in Table 2, and these particles are mixed in a sample mill at 13000 rpm for 30 seconds. This mixing procedure is repeated 3 times. As a result, the catalyst-attached resin particles CR1 to CR14 in which the photocatalyst is attached to the surfaces of the resin particles are produced.

The SEM observation indicates that, in the catalyst-attached resin particles formed by using aerogel particles as photocatalyst particles, the photocatalyst particles in the form of aggregates having an aerogel structure are attached to the surface of the resin particle. The SEM observation also indicates that, in the catalyst-attached resin particles formed by using particles other than aerogel particles as photocatalyst particles, the photocatalyst particles in the form of primary particles are attached to the surface of the resin particle.

The following characteristics of the obtained catalyst-attached resin particles are measured in accordance with the foregoing methods. The catalyst-attached resin particles are listed in Table 2.

Coverage of photocatalyst particles on resin particles

Proportion of photocatalyst particles released from resin particles

Production of Filters

The following holding members having a filter function are prepared.

Holding member BM1 (trade name "polypropylene melt-blown nonwoven fabric" (available from Kuraray Co., Ltd.), size: 5.5 cm long×5.5 cm wide×2 sheets, average opening diameter=2.5 μm, average fiber diameter 3.0 μm, weight 20 g/$cm^2$, thickness 0.2 mm)

Holding member BM2 (trade name "polybutylene terephthalate melt-blown nonwoven fabric" (available from Kuraray Co., Ltd.), size: 5.5 cm long×5.5 cm wide×2 sheets, average opening diameter=0.8 μm, average fiber diameter 1.0 μm, weight 30 g/$cm^2$, thickness 0.3 mm)

Holding member BM3 (trade name "polybutylene terephthalate melt-blown nonwoven fabric" (available from Kuraray Co., Ltd.), size: 5.5 cm long×5.5 cm wide×2 sheets, average opening diameter=8.5 μm, average fiber diameter 5.0 μm, weight 20 g/$cm^2$, thickness 0.3 mm)

One holding member is attached to one side of a plastic frame body (5.5 cm long×5.5 cm wide×1.0 cm thick, frame width 0.3 cm). The catalyst-attached resin particles are enclosed in the frame body, and another holding member is then attached to the other side of the frame body. The filters FT1 to FT20 with the combinations of the type and amount of the catalyst-attached resin particles and the holding member shown in Table 3 are produced accordingly.

Production of Comparative Filters
Comparative Filter CFT01

A photocatalyst particle dispersion (1 g) prepared by dispersing 1 part of metatitanic acid particles MTA1 in 9 parts of silicone resin KR-400 (available from Shin-Etsu Chemical Co., Ltd.) is sprayed onto the surface of a corrugated honeycomb filter substrate (available from Shin Nippon Feather Core Co., Ltd., (base paper: calcium carbonate paper, basis weight: 135 g/m², thickness: 0.22 mm), number of cells: 140 cells/in²) that has been processed so as to have a size of 5.5 cm long×5.5 cm wide×1.0 cm thick. The photocatalyst particle dispersion is dried at 120° C. for 8 hours to produce a filter CFT01 having a photocatalyst particle-containing resin layer on the filter surface.

Comparative Filter CFT02

A filter CFT02 having a photocatalyst particle-containing resin layer on the filter surface is produced in the same manner as for CFT01 except that, in the comparative filter CFT01, the amount of the metatitanic acid particles MTA1 is changed to 3 parts and the amount of the silicone resin KR-400 is changed to 7 parts.

Comparative Filter CFT03

A photocatalyst particle dispersion is prepared by mixing 5 parts of the metatitanic acid particles MTA1 and 5 parts of the silicone resin KR-400, which are the same materials as those of the comparative filter CFT01, and further 10 parts of toluene, which is a solvent. The photocatalyst particle dispersion (2 g) is sprayed onto the surface of the same filter substrate as that in CFT01. The photocatalyst particle dispersion is dried at 120° C. for 8 hours to produce a filter CFT03 having a photocatalyst particle-containing resin layer on the filter surface. However, the detachment of the photocatalyst particle-containing resin layer is observed on the filter surface of the filter CFT03, and the filter surface thus fails to stably carry the photocatalyst particles. The characteristics and the deodorizing performance are not evaluated.

Evaluation
Evaluation of Characteristics

The following characteristics of the obtained filters are measured in accordance with the foregoing methods.

Air permeability (cm³/cm²·sec) of filter
Visible light transmittance (%) of filter Evaluation of Deodorizing Performance The deodorizing performance of the filter is evaluated in accordance with the following method.

A visible light-type photocatalyst air cleaning device is produced by replacing LEDs for ultraviolet radiation on the upper and lower sides (upper side: three near-ultraviolet LEDs with wavelength of 365 nm, lower side: one deep ultraviolet LED with wavelength of 275 nm) in a commercial compact air cleaner LED PURE AH1 (available from Nitride Semiconductor Co., Ltd.) with LEDs for visible-light radiation (constant current driver-embedded triple white LED module AE-LED1X3-12V (available from Akizuki Denshi Tsusho Co., Ltd.)).

The filters FT1 to FT20 and CFT01 to CFT02 according to Examples are set at a predetermined position (deodorizing filter installation position) in the visible light-type photocatalyst air cleaning device. The visible light-type photocatalyst air cleaning device is then placed in an acrylic resin vacuum desiccator with a volume of 10 L, and the acrylic resin vacuum desiccator is sealed. Subsequently, ammonia gas is introduced into the desiccator through a vacuum valve until the initial concentration of ammonia gas in the desiccator reaches 300 ppm, and the air cleaning device is operated. The air in the vacuum desiccator is sampled at predetermined time intervals. The concentration of ammonia gas is measured with an ammonia gas detector tube, and the deodorizing performance is evaluated.

The evaluation criteria are as described below.
A: The concentration of ammonia gas after 120 minutes is less than 1 ppm.
B: The concentration of ammonia gas after 120 minutes is 1 ppm or more and less than 5 ppm.
C: The concentration of ammonia gas after 120 minutes is 5 ppm or more and less than 10 ppm.
D: The concentration of ammonia gas after 120 minutes is 10 ppm or more and less than 50 ppm.
E: The concentration of ammonia gas after 120 minutes is 50 ppm or more.

Evaluation of Detachment of Photocatalyst Particles

The proportion of the photocatalyst particles detached from the filter is evaluated in accordance with the following method.

The Ti element content of the photocatalyst-attached resin particles before evaluation of the deodorizing performance and after evaluation of the deodorizing performance (after 120 minutes) is measured with fluorescent X-rays, and the proportion of detached photocatalyst particles is evaluated.

Proportion (%) of detached photocatalyst particles=
(Ti element content before evaluation of deodorizing performance−Ti element content after evaluation of deodorizing performance)/Ti element content before evaluation of deodorizing performance×100

The evaluation criteria are as described below.
A: The proportion of detached photocatalyst particles is less than 5%.
B: The proportion of detached photocatalyst particles is 5% or more and less than 10%.
C: The proportion of detached photocatalyst particles is 10% or more and less than 20%.
D: The proportion of detached photocatalyst particles is 20% or more and less than 30%.
E: The proportion of detached photocatalyst particles is 30% or more.

The details and the evaluation results of the filters are summarized in Table 3.

TABLE 1

| Photocatalyst Particles | Particle Size DC (µm) | Visi Characteristics | | | IR Characteristics |
|---|---|---|---|---|---|
| | | Absorbance at Wavelength of 450 nm | Absorbance at Wavelength of 600 nm | Absorbance at Wavelength of 750 nm | Wavenumber of Absorption Peak (cm⁻¹) |
| Metatitanic Acid Particles MTA1 | 0.042 | 0.63 | 0.46 | 0.29 | 2850/2920 |
| Metatitanic Acid Particles MTA2 | 0.095 | 0.58 | 0.42 | 0.23 | 2854/2924 |
| Metatitanic Acid Particles MTA3 | 0.150 | 0.44 | 0.30 | 0.19 | 2848/2918 |
| Titanium Oxide Particles TO1 | 0.010 | 0.62 | 0.37 | 0.28 | 2849/2917 |
| Titanium Oxide Particles TO2 | 0.020 | 0.55 | 0.33 | 0.21 | 2853/2917 |

TABLE 1-continued

| | Photocatalyst Particles | Visi Characteristics | | | IR Characteristics |
|---|---|---|---|---|---|
| | Particle Size DC (μm) | Absorbance at Wavelength of 450 nm | Absorbance at Wavelength of 600 nm | Absorbance at Wavelength of 750 nm | Wavenumber of Absorption Peak (cm⁻¹) |
| Titanium Oxide Particles TO3 | 0.450 | 0.35 | 0.21 | 0.10 | 2852/2919 |
| Titanium Oxide Aerogel Particles TOAG1 | 0.080 | 0.60 | 0.37 | 0.25 | 2855/2920 |
| Silica-Titania Composite Aerogel Particles STAG1 | 0.024 | 0.24 | 0.15 | 0.06 | 2847/2921 |
| Silica-Titania Composite Aerogel Particles STAG2 | 0.056 | 0.25 | 0.16 | 0.06 | 2851/2923 |

TABLE 2

| Catalyst-Attached Resin Particles | Resin Particles | | | Photocatalyst Particles | | | | Proportion (%) of Released Photocatalyst Particles | Particle Size Ratio DC/DR |
|---|---|---|---|---|---|---|---|---|---|
| | Type | Particle Size DR (μm) | Amount (number of parts) | Type | Particle Size DC (μm) | Amount (number of parts) | Coverage (%) | | |
| CR1 | Silicone-based resin particles SR1 | 13.5 | 100 | Metatitanic acid particles MTA1 | 0.042 | 1.6 | 85 | 15 | 0.003 |
| CR2 | Silicone-based resin particles SR2 | 5.0 | 100 | Titanium oxide particles TO1 | 0.010 | 1.4 | 72 | 28 | 0.002 |
| CR3 | Silicone-based resin particles SR1 | 13.5 | 100 | Titanium oxide aerogel particles TOAG1 | 0.080 | 3.0 | 70 | 23 | 0.006 |
| CR4 | Silicone-based resin particles SR2 | 5.0 | 100 | Silica-titania composite aerogel particles STAG1 | 0.024 | 2.0 | 75 | 18 | 0.005 |
| CR5 | Silicone-based resin particles SR1 | 13.5 | 100 | Silica-titania composite aerogel particles STAG2 | 0.056 | 1.7 | 73 | 20 | 0.004 |
| CR6 | Crosslinked PMMA particles MMA1 | 11.0 | 100 | Metatitanic acid particles MTA1 | 0.042 | 3.8 | 88 | 9 | 0.004 |
| CR7 | Crosslinked PMMA particles MMA1 | 11.0 | 100 | Titanium oxide particles TO1 | 0.010 | 1.2 | 72 | 35 | 0.001 |
| CR8 | Crosslinked styrene particles ST1 | 3.5 | 100 | Metatitanic acid particles MTA1 | 0.042 | 10.0 | 68 | 30 | 0.012 |
| CR9 | Crosslinked PMMA particles MMA2 | 18.5 | 100 | Metatitanic acid particles MTA1 | 0.042 | 2.2 | 70 | 24 | 0.002 |
| CR10 | Crosslinked PMMA particles MMA2 | 18.5 | 100 | Metatitanic acid particles MTA2 | 0.095 | 5.0 | 69 | 27 | 0.005 |
| CR11 | Crosslinked PMMA particles MMA2 | 18.5 | 100 | Metatitanic acid particles MTA3 | 0.150 | 8.0 | 66 | 32 | 0.008 |
| CR12 | Silicone-based resin particles SR3 | 0.7 | 100 | Titanium oxide particles TO2 | 0.020 | 15.0 | 48 | 45 | 0.029 |
| CR13 | Crosslinked styrene particles ST2 | 49.5 | 100 | Titanium oxide particles TO3 | 0.450 | 12.0 | 52 | 43 | 0.009 |
| CR14 | Silicone-based resin particles SR2 | 5.0 | 100 | Titanium oxide particles TO3 | 0.450 | 50.0 | 35 | 55 | 0.09 |

TABLE 3

| Filter | Catalyst-Attached Resin Particles | | Holding Member Type | Characteristics | | Evaluation | | Note |
|---|---|---|---|---|---|---|---|---|
| | Type | Amount (g) | | Air Permeability (cm³/cm² sec) | Visible Light Transmittance (%) | Deodorizing Performance | Detachment of Photocatalyst Particles | |
| FT1 | CR1 | 7.5 | BM1 | 90 | 63 | A | A | Example |
| FT2 | CR2 | 7.5 | BM1 | 70 | 60 | B | A | Example |
| FT3 | CR3 | 7.5 | BM1 | 85 | 65 | B | A | Example |
| FT4 | CR4 | 7.5 | BM1 | 72 | 58 | B | A | Example |
| FT5 | CR5 | 7.5 | BM1 | 95 | 62 | A | A | Example |
| FT6 | CR6 | 7.5 | BM1 | 77 | 63 | A | A | Example |
| FT7 | CR7 | 7.5 | BM1 | 75 | 60 | B | B | Example |
| FT8 | CR8 | 7.5 | BM2 | 60 | 54 | B | B | Example |
| FT9 | CR9 | 7.5 | BM3 | 120 | 65 | B | B | Example |
| FT10 | CR10 | 7.5 | BM3 | 130 | 63 | B | B | Example |
| FT11 | CR11 | 7.5 | BM3 | 115 | 66 | C | B | Example |
| FT12 | CR12 | 7.5 | BM2 | 40 | 58 | C | C | Example |
| FT13 | CR13 | 7.5 | BM3 | 180 | 68 | C | C | Example |

TABLE 3-continued

| Filter | Catalyst-Attached Resin Particles Type | Amount (g) | Holding Member Type | Characteristics Air Permeability (cm³/cm·sec) | Visible Light Transmittance (%) | Evaluation Deodorizing Performance | Detachment of Photocatalyst Particles | Note |
|---|---|---|---|---|---|---|---|---|
| FT14 | CR14 | 7.5 | BM1 | 72 | 62 | B | C | Example |
| FT15 | CR1 | 10 | BM1 | 55 | 50 | A | A | Example |
| FT16 | CR2 | 10 | BM1 | 45 | 45 | B | B | Example |
| FT17 | CR3 | 10 | BM1 | 52 | 52 | B | B | Example |
| FT18 | CR4 | 10 | BM1 | 45 | 46 | A | A | Example |
| FT19 | CR5 | 10 | BM1 | 60 | 52 | A | B | Example |
| FT20 | CR6 | 10 | BM1 | 48 | 49 | A | A | Example |
| CFT01 | metatitanic acid particles MTA1/silicone resin | | | >300 | 75 | E | — | Comparative Example |
| CFT02 | metatitanic acid particles MTA1/silicone resin | | | >300 | 75 | D | — | Comparative Example |
| CFT03 | metatitanic acid particles MTA1/silicone resin | | | not evaluated | | | | Comparative Example |

The foregoing results indicate that the filters according to Examples have higher deodorizing performance than the filters according to Comparative Examples.

The foregoing description of the exemplary embodiments of the present disclosure has been provided for the purposes of illustration and description. It is not intended to be exhaustive or to limit the disclosure to the precise forms disclosed. Obviously, many modifications and variations will be apparent to practitioners skilled in the art. The embodiments was/were chosen and described in order to best explain the principles of the disclosure and its practical applications, thereby enabling others skilled in the art to understand the disclosure for various embodiments and with the various modifications as are suited to the particular use contemplated. It is intended that the scope of the disclosure be defined by the following claims and their equivalents.

What is claimed is:

1. A filter comprising:
   resin particles;
   photocatalyst particles having absorption at wavelengths of 450 nm and 750 nm in a visible absorption spectrum, wherein the photocatalyst particles are present on a surface of each resin particle, and at least a portion of a surface of each of the photocatalyst particles is attached to an organometallic compound, and
   a holding member that holds the photocatalyst-attached resin particles inside, the holding member being a bag-shaped member or a box-shaped member.

2. The filter according to claim 1, wherein the photocatalyst particles have absorption in an entire wavelength range from 400 nm to 800 nm in the visible absorption spectrum.

3. The filter according to claim 1, wherein the photocatalyst particles have an absorption peak in a range from 2700 $cm^{-1}$ to 3000 $cm^{-1}$ in an infrared absorption spectrum.

4. The filter according to claim 1, wherein the photocatalyst particles are at least one selected from the group consisting of metatitanic acid particles, titanium oxide particles, titanium oxide aerogel particles, and silica-titania composite aerogel particles.

5. The filter according to claim 1, wherein the photocatalyst particles have an average particle size in a range from 0.01 μm to 0.5 μm.

6. The filter according to claim 1, wherein the photocatalyst particles have an average particle size in a range from 0.02 μm to 0.15 μm.

7. The filter according to claim 1, wherein the resin particles have an average particle size in a range from 0.5 μm to 50 μm.

8. The filter according to claim 1, wherein the resin particles have an average particle size in a range from 3 μm to 20 μm.

9. The filter according to claim 1, wherein a ratio of an average particle size of the photocatalyst particles to an average particle size of the resin particles is in a range from 0.001 to 0.1.

10. The filter according to claim 1, wherein a ratio of an average particle size of the photocatalyst particles to an average particle size of the resin particles is in a range from 0.002 to 0.05.

11. The filter according to claim 1, wherein a coverage of the photocatalyst particles on the resin particles is in a range from 30% to 100%.

12. The filter according to claim 1, wherein a coverage of the photocatalyst particles on the resin particles is in a range from 50% to 100%.

13. The filter according to claim 1, wherein the resin particles are at least one selected from silicone resin particles, crosslinked styrene resin particles, and crosslinked acrylic resin particles.

14. The filter according to claim 1, wherein the resin particles are silicone resin particles, and the photocatalyst particles are metatitanic acid particles.

15. The filter according to claim 1, wherein the holding member is air permeable.

16. The filter according to claim 1, wherein the photocatalyst particles are selected from the group consisting of titanium oxide particles, titanium oxide aerogel particles, and silica-titania composite aerogel particles.

17. The filter according to claim 1, wherein the absorption at the wavelength of 450 nm is 0.2 or more.

* * * * *